US008377866B2

(12) United States Patent
Yoon et al.

(10) Patent No.: US 8,377,866 B2
(45) Date of Patent: Feb. 19, 2013

(54) ANTIMICROBIAL PROTEIN DERIVED FROM PODOVIRIDAE BACTERIOPHAGE SPECIFIC TO *STAPHYLOCOCCUS AUREUS*

(75) Inventors: Seongjun Yoon, Seoul (KR); Yunjaie Choi, Seoul (KR); Seyung Lee, Pyeongtaek-si (KR); Jeesoo Son, Seoul (KR); Sooyoun Jun, Seoul (KR); Sanghyeon Kang, Seoul (KR)

(73) Assignee: Intron Biotechnology, Inc., Sungnam-Si (KR)

( * ) Notice: Subject to any disclaimer, the term of this patent is extended or adjusted under 35 U.S.C. 154(b) by 827 days.

(21) Appl. No.: 12/378,365

(22) Filed: Feb. 12, 2009

(65) Prior Publication Data
US 2010/0203180 A1 Aug. 12, 2010

(51) Int. Cl.
*A61K 38/16* (2006.01)
(52) U.S. Cl. .................... 514/1.1; 424/780; 435/252.33; 530/350; 536/23.72
(58) Field of Classification Search .................... None
See application file for complete search history.

(56) References Cited

U.S. PATENT DOCUMENTS

| | | | | |
|---|---|---|---|---|
| 6,056,954 | A | 5/2000 | Fischetti | 424/94.1 |
| 6,056,955 | A | 5/2000 | Fischetti | |
| 6,121,036 | A | 9/2000 | Ghanbari | 436/69.3 |
| 6,264,945 | B1 | 7/2001 | Fischetti | 424/94.1 |
| 6,432,444 | B1 | 8/2002 | Fischetti et al. | 424/443 |
| 2003/0152594 | A1 | 8/2003 | Pillich | 424/243.1 |
| 2003/0216338 | A1 | 11/2003 | Merril | 436/235.1 |
| 2004/0091470 | A1 | 5/2004 | Fischetti et al. | 424/94.6 |
| 2005/0260171 | A1 | 11/2005 | Ghanbari et al. | 424/630 |
| 2010/0144619 | A1 | 6/2010 | Yoon et al. | 514/2.7 |
| 2010/0203019 | A1 | 8/2010 | Yoon et al. | 424/93.6 |
| 2010/0254950 | A1* | 10/2010 | Yoon et al. | 424/93.6 |
| 2010/0267117 | A1 | 10/2010 | Yoon et al. | 435/6 |

FOREIGN PATENT DOCUMENTS

| | | |
|---|---|---|
| KR | 2006-55461 | 6/2006 |
| KR | 2006-73562 | 8/2006 |
| KR | 2007-02358 | 8/2007 |
| KR | 2007-82357 | 2/2009 |
| WO | WO 03/067991 | 8/2003 |
| WO | WO 2004/020451 | 3/2004 |
| WO | WO 2004/062677 | 7/2004 |
| WO | WO 2006/063176 | 6/2006 |
| WO | WO2007/148919 | 12/2007 |
| WO | WO2008/016240 | 2/2008 |
| WO | WO 2008/035303 | * 3/2009 |
| WO | WO 2009/035303 | 3/2009 |

OTHER PUBLICATIONS

KCTC 11152BP, *Escherichia coli* pBAD::Lysin, 2007.
KCTC 11153BP, SAP1 bacteriophage, 2007.
KCTC 11154BP, SAP2 bacteriophage, 2007.
KACC 97001P, *Staphlococcal* bacterophage JS, 2006.
Vybiral D, Talcác M, Loessner M, Witte A, von Ahsen U, Bläsi U. (2003) Complete nucleotide sequence and molecular characterization of two lytic *Staphylococcus aureus* phages: 44AHJD and P68. FEMS Microbiol Lett. 219(2): 275-283.
Arciola CR, Baldassarri L, Montanaro L. (2001) Presence of icaA and icaD genes and slime production in a collection of staphylococcal strains from catheter-associated infections. J Clin Microbiol. 39(6): 2151-2156.
Arciola CR, Montanaro L, Baldassarri L, Borsetti E, Cavedagna D, Donati E. (1999) Slime production by Staphylococci isolated from prosthesis-associated infections. New Microbiol. 22(4): 337-341.
Bernhardt TG, Wang IN, Struck DK, Young R. (2002) Breaking free: "protein antibiotics" and phage lysis. Res Microbiol. 153(8): 493-501.
Bokarewa MI, Jin T, Tarkowski A. (2006) *Staphylococcus aureus*: Staphylokinase. Int J Biochem Cell Biol. 38(4): 504-509.
Cisani G, Varaldo PE, Grazi G, Soro O. (1982) High-level potentiation of lysostaphin anti-staphylococcal activity by lysozyme. Antimicrob Agents Chemother. 21(4): 531-535.
Costerton JW, Lewandowski Z, DeBeer D, Caldwell D, Korber D, James G. (1994) Biofilms, the customized microniche. J Bacteriol. 176(8): 2137-2142.
Cramton SE, Gerke C, Schnell NF, Nichols WW, Götz F. (1999) The intercellular adhesion (ica) locus is present in *Staphylococcus aureus* and is required for biofilm formation. Infect Immun. 67(10): 5427-5433.
Genbank Accession No. AA047477, titled "Soares pregnant uterus NbHPU", entered Sep. 19, 1996.
Genbank Accession No. AY176327, titled "*Staphylococcus* phage K, complete genome", Direct Submission (See O'Flaherty et al., 2004).
GenBank Accession No. AY954969, titled "Bacteriophage G1, complete genome", Direct Submission (See Kwan et al., 2005).
Graham S, Coote PJ. (2007) Potent, synergistic inhibition of *Staphylococcus aureus* upon exposure to a combination of the endopeptidase lysostaphin and the cationic peptide ranalexin. J Antimicrob Chemother. 59(4): 759-762.
Gründling A, Missiakas DM, Schneewind O. (2006) *Staphylococcus aureus* mutants with increased lysostaphin resistance. J Bacteriol. 188(17): 6286-6297.
Kusuma C, Jadanova A, Chanturiya T, Kokai-Kun JF. (2007) Lysostaphin-resistant variants of *Staphylococcus aureus* demonstrate reduced fitness in vitro and in vivo. Antimicrob Agents Chemother. 51(2): 475-482.
Kwan T, Liu J, DuBow M, Gros P, Pelletier J. (2005) The complete genomes and proteomes of 27 *Staphylococcus aureus* bacteriophages. Proc Natl Acad Sci USA. 102(14): 5174-5179.

(Continued)

Primary Examiner — Christopher R. Tate
Assistant Examiner — Roy Teller
(74) Attorney, Agent, or Firm — Ballard Spahr LLP

(57) ABSTRACT

The present invention relates to a novel antimicrobial protein derived from bacteriophage having killing activity specific to *Staphylococcus aureus*, more precisely an antimicrobial protein originated from Podoviridae bacteriophage having killing activity specific to *Staphylococcus aureus* which is the causing agent of infectious disease in human and animals, a pharmaceutical composition for the prevention and treatment of infectious disease caused by *Staphylococcus aureus*, an antibiotic and a disinfectant containing the bacteriophage-originated antimicrobial protein as an active ingredient.

10 Claims, 5 Drawing Sheets

OTHER PUBLICATIONS

Loessner MJ, Gaeng S, Scherer S. (1999) Evidence for a holin-like protein gene fully embedded out of frame in the endolysin gene of *Staphylococcus aureus* bacteriophage 187. J Bacteriol. 181(15): 4452-4460.

Loessner MJ. (2005) Bacteriophage endolysins—current state of research and applications. Curr Opin Microbiol. 8(4): 480-487.

Mah TF, O'Toole GA. (2001) Mechanisms of biofilm resistance to antimicrobial agents. Trends Microbiol. 9(1): 34-39.

Matsuzaki S, Rashel M, Uchiyama J, Sakurai S, Ujihara T, Kuroda M, Ikeuchi M, Tani T, Fujieda M, Wakiguchi H, Imai S. (2005) Bacteriophage therapy: a revitalized therapy against bacterial infectious diseases. J Infect Chemother. 11(5): 211-219.

Matsuzaki S, Yasuda M, Nishikawa H, Kuroda M, Ujihara T, Shuin T, Shen Y, Jin Z, Fujimoto S, Nasimuzzaman MD, Wakiguchi H, Sugihara S, Sugiura T, Koda S, Muraoka A, Imai S. (2003) Experimental protection of mice against lethal *Staphylococcus aureus* infection by novel bacteriophage phi MR11. J Infect Dis. 187(4): 613-624.

McKenney D, Pouliot KL, Wang Y, Murthy V, Ulrich M, Döring G, Lee JC, Goldmann DA, Pier GB. (1999) Broadly protective vaccine for *Staphylococcus aureus* based on an in vivo-expressed antigen. 284(5419): 1523-1527.

O'Flaherty S, Coffey A, Edwards R, Meaney W, Fitzgerald GF, Ross RP. (2004) Genome of staphylococcal phage K: a new lineage of Myoviridae infecting gram-positive bacteria with a low G+C content. J Bacteriol. 186(9): 2862-2871.

O'Gara JP, Humphreys H. (2001) *Staphylococcus epidermidis* biofilms: importance and implications. J Med Microbiol. 50(7): 582-587.

Resch A, Fehrenbacher B, Eisele K, Schaller M, Götz F. (2005) Phage release from biofilm and planktonic *Staphylococcus aureus* cells. FEMS Microbiol Lett. 252(1): 89-96.

Sass P, Bierbaum G. (2007) Lytic activity of recombinant bacteriophage phi11 and phi12 endolysins on whole cells and biofilms of *Staphylococcus aureus*. Appl Environ Microbiol. 73(1): 347-352.

Schuch R, Nelson D, Fischetti VA. (2002) A bacteriolytic agent that detects and kills *Bacillus anthracis*. Nature. 418(6900): 884-889.

Severance PJ, Kauffman CA, Sheagren JN. (1980) Rapid identification of *Staphylococcus aureus* by using lysostaphin sensitivity. J Clin Microbiol. 11(6): 724-727.

Skurnik M, Strauch E. (2006) Phage therapy: facts and fiction. Int J Med Microbiol. 296(1): 5-14.

Waldvogel FA. (2000) Infections Associated with Indwelling Medical Devices, pp. 55-88, 2000, ASM, Washington, DC.

Walencka E, Sadowska B, Rózalska S, Hryniewicz W, Rózalska B. (2006) *Staphylococcus aureus* biofilm as a target for single or repeated doses of oxacillin, vancomycin, linezolid and/or lysostaphin. Folia Microbiol (Praha). 51(5): 381-386.

Wu JA, Kusuma C, Mond JJ, Kokai-Kun JF. (2003) Lysostaphin disrupts *Staphylococcus aureus* and *Staphylococcus epidermidis* biofilms on artificial surfaces. Antimicrob Agents Chemother. 47(11): 3407-3414.

Yoong P, Schuch R, Nelson D, Fischetti VA. (2004) Identification of a broadly active phage lytic enzyme with lethal activity against antibiotic-resistant *Enterococcus faecalis* and *Enterococcus faecium*. J Bacteriol. 186(14): 4808-4812.

Written Opinion issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Search Report issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Preliminary Report on Patentability issued Mar. 16, 2010 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

Preliminary Amendment filed Mar. 12, 2010 for U.S. Appl. No. 12/677,990 filed on Mar. 12, 2010 (Inventors—Yoon et al.).

Written Opinion issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

International Search Report issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

International Preliminary Report on Patentability issued Feb. 10, 2009 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

Written Opinion issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Search Report issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Preliminary Report on Patenability issued Dec. 22, 2008 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

Notice of Allowance with Examiner Interview Summary issued Jun. 1, 2011 for U.S. Appl. No. 12/378,457, filed Feb. 12, 2009 (Inventors—Yoon et al.).

Final Rejection issued Apr. 28, 2011 for U.S. Appl. No. 12/378,457, filed Feb. 12, 2009 (Inventors—Yoon et al.).

Response after Non-Final Office Action filed Feb. 25, 2011 for U.S. Appl. No. 12/378,457, filed Feb. 12, 2009 (Inventors—Yoon et al.).

Non-Final Rejection issued Oct. 26, 2010 for U.S. Appl. No. 12/378,457, filed Feb. 12, 2009 (Inventors—Yoon et al.).

Preliminary Amendment filed Dec. 19, 2008 for U.S. Appl. No. 12/308,627, filed Jun. 15, 2009 (Inventors—Yoon et al.).

Response to Non-Final Office Action filed Jul. 5, 2011 for U.S. Appl. No. 12/308,622, filed May 27, 2009 (Inventors—Yoon et al.).

Non-Final Office Action issued Mar. 3, 2011 for U.S. Appl. No. 12/308,622, filed May 27, 2009 (Inventors—Yoon et al.).

Preliminary Amendment filed Dec. 19, 2008 for U.S. Appl. No. 12/308,622, filed May 27, 2009 (Inventors—Yoon et al.).

Notice of Allowance mailed Aug. 3, 2012 for U.S. Appl. No. 12/677,990, filed Mar. 12, 2010 (Yoon et al.—Inventors) (13 pages).

Issue Notification mailed Jul. 11, 2012 for U.S. Appl. No. 12/308,627, filed Jun. 15, 2009 (Yoon et al.—Inventors) (1 page).

Response to Rule 312 Amendment mailed Jul. 6, 2012 for U.S. Appl. No. 12/308,627, filed Jun. 15, 2009 (Yoon et al.—Inventors) (2 pages).

Amendment in Response to Notice to File Corrected Application Papers mailed Jun. 29, 2012 for U.S. Appl. No. 12/308,627, filed Jun. 15, 2009 (Yoon et al.—Inventors) (4 pages).

Response to Notice to File Corrected Application Papers mailed Jun. 29, 2012 for U.S. Appl. No. 12/308,627, filed Jun. 15, 2009 (Yoon et al.—Inventors) (5 pages).

Issue Notification mailed Nov. 16, 2011 for U.S. Appl. No. 12/308,622.

Notice of Allowance mailed Sep. 20, 2011 for U.S. Appl. No. 12/308,622.

Notice of Allowance mailed Apr. 3, 2012 for U.S. Appl. No. 12/308,627.

Response after Non-Final Action filed Feb. 1, 2012 for U.S. Appl. No. 12/308,627.

Non-Final Rejection mailed Sep. 1, 2011 for U.S. Appl. No. 12/308,627.

Issue Notification mailed Oct. 5, 2011 for U.S. Appl. No. 12/378,457.

Notice of Allowance mailed Aug. 8, 2011 for U.S. Appl. No. 12/378,457.

Response to Election / Restriction filed May 2, 2012 for U.S. Appl. No. 12/677,990.

Restriction Requirement mailed Feb. 21, 2012 for U.S. Appl. No. 12/677,990.

\* cited by examiner

Phage gDNA partial digestion → 3-10kb gel elution

Phage genomic library construction

Sequence analysis

ANTIMICROBIAL PROTEIN DERIVED FROM PODOVIRIDAE BACTERIOPHAGE SPECIFIC TO *STAPHYLOCOCCUS AUREUS*

TECHNICAL FIELD

The present invention relates to a novel antimicrobial protein derived from Podoviridae bacteriophage having killing activity (lytic activity, antimicrobial activity) specific to *Staphylococcus aureus*.

BACKGROUND ART

Bacteriophage is a kind of virus-like microorganism infecting bacteria and generally called 'phage' in short. Bacteriophage is an organism having a simple structure wherein a central genetic material composed of nucleic acid is covered by a protein envelope. The nucleic acid is single stranded or double stranded DNA or RNA. To survive, bacteriophage needs a host bacterium and every bacterium has a specific partner bacteriophage. When bacteriophage invades into a host bacterium, it multiplicates itself and then induces expressions of enzymes involved in the decomposition of cell wall of the host bacterium. The enzymes destroy cell wall by attacking the peptidoglycan layer which is responsible for rigidity and mechanical strength of cell wall.

Bacteriophage was first found by Twort, an English bacteriologist, in 1915 during his research on the phenomenon that micrococcus colony is decomposed turning transparent by something. And in 1917, a French bacteriologist d'Herelle found out that there was something that decomposes *Shigella disentriae* in filtrate of feces of a patient with dysentery, and he continued to study to identify the material, leading to the finding of bacteriophage which means "eating bacteria". Since then, bacteriophages against *Shigella dysenteriae*, *Salmonella typhi*, and *Vibrio cholerae* were further identified. Since penicillin was found by Flemming in 1950, antibiotics have been widely used and the study on bacteriophage continued only in some East European countries and it became out of concern in many other countries. However, since 2000, multidrug-resistant pathogenic bacteria resulted from overuse and/or mis-use of antibiotics have been frequently reported. Because of potential as an alternative for the conventional antibiotics, bacteriophage became in the spotlight again and the studies on bacteriophage are actively undergoing led by advanced countries.

Even though antibiotics (or antibacterial agents) are still major therapeutic agents for the treatment of various infectious diseases, it has been a serious problem since 1980s that the excessive use of such antibiotics generates numbers of multi-drug resistant strains. In 1986, *Staphylococcus aureus* having resistance against vancomycin, which is so called 'the drug of last resort', and other multi-drug resistant strains were found, giving a great shock to those in medical field. Vancomycin resistant enterococci (VRE) were first reported in France in 1986 and first separated in USA in 1988. Since then, the cases of VRE infection have been increased every year with high frequency, everywhere including Europe, USA, Singapore, Japan, Australia, Korea, etc, making the VRE as a causal agent of nosocomial infections. In Korea, VRE was first isolated in 1992. As for *Staphylococcus aureus*, vancomycin-resistant *Staphylococcus aureus* (VRSA) was first found in the early 1990s and was first found in Korea in June, 1996.

Therefore, it is an urgent request to develop a novel antibiotic to treat the infectious diseases caused by bacteria resistant against conventional antibiotics and further to lead national health and medical techniques. Again, it is urgently required to develop an alternative antibiotic to solve the problems of multi-drug resistant bacteria along with the abuse or misuse of the conventional antibiotics and the bio-accumulation of antibiotics. To solve the problem of such resistant bacteria, an alternative antibiotic has to be developed by a completely and fundamentally different method.

The present inventors isolated novel bacteriophage capable of killing specifically *Staphylococcus aureus*, and deposited the bacteriophage at Korean Agricultural Culture Collection, National Institute of Agricultural Biotechnology on Jun. 14, 2006 (Accession No: KACC 97001P) and at Biological Resource Center, Korea Research Institute of Bioscience and Biotechnology on Jul. 18, 2007 (Accession No: KCTC 11153BP). The related matters have been applied for a patent (Korean Patent Application No. 2006-55461). The present inventors continued the study and as a result isolated another effective bacteriophage, and then deposited the isolated bacteriophage at Biological Resource Center, Korea Research Institute of Bioscience and Biotechnology on Jul. 18, 2007 (Accession No: KCTC 11154BP).

Even if the said two bacteriophages are effective in prevention and treatment of infectious disease caused by *Staphylococcus aureus*, they still have a few disadvantages. Direct application of bacteriophage, which means the bacteriophage itself is directly used, raises vague aversion, leading to the limitation in use. In addition, to obtain bacteriophage for direct use massively, it is important and necessary to culture host pathogenic bacteria, indicating that there is a high chance of exposure of a worker on pathogenic bacteria. So, a very strict pathogenic bacteria regulation is required. Accordingly it is required to develop a novel substance having characteristics of bacteriophage and capable of killing *Staphylococcus aureus* in safer way and facilitating wider application.

The present inventors applied for a patent describing a novel antibacterial protein originated from the bacteriophage capable of killing specifically *Staphylococcus aureus* based on the genetic information thereon (Korean Patent Application No. 2006-73562). It was demonstrated that lytic protein had same lytic effect as that of an endogenous lytic protein in a host when it is extracellularly treated and has a broader bactericidal activity compared to the corresponding bacteriophage itself.

However, like bacteriophage, such antimicrobial proteins take different bacteria as their targets and are different in their antimicrobial spectrum. Thus, it is required to obtain in variety of antimicrobial proteins.

As described hereinbefore, lytic protein (antibacterial protein) derived from bacteriophage is a protein that destroys cell wall of a host bacterium when the bacteriophage comes out of the host bacterium. Such lytic protein derived from bacteriophage is generally called lysin. The lytic protein, lysin, is composed of N-terminal catalytic domain and C-terminal binding domain and these two domains are linked by a short linker. Lysin can have two different catalytic domains, which is a rare case, though. C-terminal binding domain is conjugated with cell wall of target bacteria. The catalytic regions of lysin are conserved when they are in the same class according to Linne's hierarchical classification system but binding domains are different. Such variability of binding domain makes difference in bacteriolytic effect among lytic proteins.

So, preparing an additional lytic protein as described in this invention paves the way to cope with more *Staphylococcus aureus* and a cocktail of those lytic proteins is expected to bring broader antimicrobial effect, compared with a single lytic protein.

DISCLOSURE

Technical Problem

The present inventors completed this invention by providing a novel antimicrobial protein having killing activity specific to *Staphylococcus aureus*, and further by confirming that this novel antimicrobial protein specific to *Staphylococcus aureus* can be effectively used for the prevention and treatment of disease caused by *Staphylococcus aureus*.

Therefore, it is an object of the present invention to provide a novel antimicrobial protein having killing activity specific to *Staphylococcus aureus*, the causing agent of infectious disease in human and animals.

It is another object of the present invention to provide a pharmaceutical composition for the prevention and treatment of infectious disease caused by *Staphylococcus aureus* containing the antimicrobial protein as an active ingredient.

It is a further object of the present invention to provide an antibiotic containing the antimicrobial protein as an active ingredient.

It is also an object of the present invention to provide a disinfectant containing the antimicrobial protein as an active ingredient.

Technical Solution

The present invention provides an antimicrobial protein having killing activity specific to *Staphylococcus aureus* and having the amino acid sequence represented by SEQ. ID. NO: 3, and a gene encoding the same.

In this description, the term 'antimicrobial activity' includes the activities resulted from lysis action and/or other antimicrobial mechanisms.

*Staphylococcus aureus* is a causing agent of skin infection and food poisoning. It was reported that *Staphylococcus aureus* isolated in Korea had resistance against methicillin as high as 73% at average, which is the top level in the world. That means 73% of *Staphylococcus aureus* cannot be killed by methicillin and this bacterium is highly antibiotic resistant.

*Staphylococcus aureus* is the number one pathogenic bacterium to cause infectious mastitis in cattle. *Staphylococcus aureus* is found in 90% of the total dairy cows in USA and the dairy cow infected by this pathogenic bacterium in total dairy cows is estimated to be 10%. *Staphylococcus aureus* is a causing agent of acute dermatitis in human, and this acute dermatitis can be suddenly developed into sepsis taking a patient's life. *Staphylococcus aureus* is also a causing agent of pyogenic disease, sweat odor and food poisoning.

The present inventors have endeavored to kill *Staphylococcus aureus* selectively. The inventors isolated *Staphylococcus aureus* from pathogen and a novel Podoviridae bacteriophage that is able to kill the isolated *Staphylococcus aureus* selectively. This novel bacteriophage having killing activity specific to *Staphylococcus aureus*, isolated by the inventors, was named 'SAP-2' and deposited at Korean Collection for Type Cultures, Korea Research Institute of Bioscience and Biotechnology on Jul. 18, 2007 (Accession No: KCTC 11154BP).

The present inventors completed this invention by providing a novel antimicrobial protein capable of killing *Staphylococcus aureus* specifically based on the genetic information of the *Staphylococcus aureus* specific bacteriophage SAP-2 (Accession No: KCTC 11154BP) and by confirming that the *Staphylococcus aureus* specific antimicrobial protein can be efficiently used for the prevention and treatment of disease caused by *Staphylococcus aureus*.

The present inventors found out a gene encoding an antimicrobial protein from the genome of the bacteriophage SAP-2, with which the inventors produced and purified an antimicrobial protein utilizing molecular biological and biotechnological techniques. The antimicrobial protein has the amino acid sequence represented by SEQ. ID. NO: 3 and the gene encoding the protein has the nucleotide sequence represented by SEQ. ID. NO: 2.

The present invention also provides an *E. coli* transformant (Accession No: KCTC 11152BP) for the production of an antimicrobial protein capable of killing *Staphylococcus aureus* specifically.

The present inventors constructed an *E. coli* transformant overexpressing the antimicrobial protein (SEQ. ID. NO: 3) and named it 'pBAD::lysinM', which was deposited at Biological Resource Center, Korea Research Institute of Bioscience and Biotechnology on Jul. 18, 2007 (Accession No: KCTC 11152BP). The said *E. coli* transformant contains a protein having excellent antimicrobial activity. Therefore, the product obtained by culturing the transformant can be effectively used for the prevention and treatment of infectious disease caused by *Staphylococcus aureus*.

The present invention also provides a pharmaceutical composition for the prevention and treatment of infectious disease caused by *Staphylococcus aureus* containing the antimicrobial protein originated from the bacteriophage SAP-2 as an active ingredient.

The term 'treatment' herein indicates (i) the prevention of the infectious disease caused by *Staphylococcus aureus*; (ii) the suppression of the infectious disease caused by *Staphylococcus aureus*; and (iii) the relief of the infectious disease caused by *Staphylococcus aureus*.

As explained hereinbefore, the antimicrobial protein included in the pharmaceutical composition of the present invention has killing activity specific to *Staphylococcus aureus*. Thus, the pharmaceutical composition of the present invention can be used for the treatment of various diseases caused by *Staphylococcus aureus* such as mastitis, acute dermatitis, sepsis, pyogenic disease, food poisoning, pneumonia, osteomyelitis, impetigo, bacteremia, endocarditis and enteritis. According to a preferred embodiment of the present invention, everyday spray of the antimicrobial protein solution of the invention on the lesion of dairy cow with mastitis could significantly reduce the symptoms of mastitis, suggesting that the antimicrobial protein of the invention is effective in the treatment of mastitis.

The pharmaceutical composition of the present invention can additionally include a pharmaceutically acceptable carrier, which is exemplified by lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but not always limited thereto. The pharmaceutical composition of the present invention can also include a lubricant, a wetting agent, a sweetener, a flavor, an emulsifier, a suspending agent, and a preservative, in addition to the above ingredients.

The pharmaceutical composition of the present invention can be applied or sprayed on the lesion, and administered orally or parenterally (for example, intravenous, intramuscular, hypodermic, local or peritoneal injection).

The effective dosage of the pharmaceutical composition of the present invention varies from the formulation, administration pathway, age, weight and gender of animal or human with a disease caused by *Staphylococcus aureus*, severity of a disease, diet, administration frequency and pathway, excretion and sensitivity. In general, the dosage can be determined by an experienced doctor with consideration of the goal of the treatment or preventive effect. In general, the pharmaceutical composition of the invention contains the antimicrobial protein at the concentration of 0.0001-10% (w/v), preferably 0.001-1% (w/v), and more preferably 0.1% (w/v).

The pharmaceutical composition of the present invention can be formulated as a unit dose medicine or as a medicine in multidose vehicle by mixing with a pharmaceutically acceptable carrier and/or excipient by the method well known to those in the art. The pharmaceutical formulation can be selected from a group consisting of ointments, solutions, suspensions or emulsions, extracts, powders, granules, tablets or capsules and additionally includes a dispersing agent or a stabilizing agent.

In another preferred embodiment of the present invention, the present invention provides an antibiotic comprising the antimicrobial protein originated from the bacteriophage SAP-2 as an active ingredient.

The term 'antibiotic' is used herein as a general term for antiseptics, bactericidal agents and antibacterial agents.

*Staphylococcus aureus* is frequently found in cosmetics along with *Bacillus subtilis*, *E. coli* and *Pseudomonas aeruginosa*. Cosmetics use oil or water as a major ingredient, to which glycerin and sorbitol, which are carbon sources of a microorganism, and amino acid derivatives and a protein which are nitrogen sources of a microorganism, are added, suggesting that there are enough nutrition and ingredients to attract microorganisms including bacteria. In addition, the term of use of the cosmetics is comparatively long, indicating that it is in high risk of contamination by a microorganism. To prevent color changes or odor changes caused by the contamination of a microorganism, an antibacterial agent is necessarily added to cosmetics for a long shelf-life.

A synthetic antiseptic such as parabens is widely used as an additive for cosmetics, but it is potentially dangerous. Particularly, since its accumulation in breast cancer cells was detected, it has been recognized that the accumulation of such synthetic antiseptic via cosmetics might be very harmful. The American Academy of Dermatology's Committee listed the synthetic antiseptic as the number two allergen causing skin trouble. Recently what worries us is that cosmetics for children also includes such artificial synthetic antiseptic, suggesting that children are exposed on such harmful antiseptic longer and much, raising the risk seriously. Therefore, it is sincerely requested to develop a natural antiseptic.

The antimicrobial protein originated from the bacteriophage SAP-2 of the present invention is characterized by its high specificity to *Staphylococcus aureus*, compared with other conventional antibiotics. That is, the antimicrobial protein originated from the bacteriophage can selectively kill *Staphylococcus aureus* only without killing useful bacteria, suggesting that it is a highly valuable antibiotic that has fewer side effects. The antimicrobial protein of the present invention is effective against wider variety of *Staphylococcus aureus* than the bacteriophage itself where the protein is derived (that is, the antimicrobial protein has broad activity spectrum).

The bacteriophage SAP-2 originated antimicrobial protein-based antibiotics, unlike the conventional antibiotics, do not induce resistance so that their life cycles are comparatively long. Most conventional antibiotics are gradually limited in use because of the increasing resistance. On the other hand, the antibiotic containing the antimicrobial protein of the invention as an active ingredient can solve the problem of the antibiotic-resistance and thus has longer life cycling. Therefore, the antibiotic containing the antimicrobial protein of the invention as an active ingredient that is able to kill *Staphylococcus aureus* selectively can be effectively used as a novel antibiotic with excellent antibacterial, bactericidal and antiseptic effects.

In another preferred embodiment of the present invention, the present invention provides a disinfectant comprising the antimicrobial protein originated from the bacteriophage SAP-2 as an active ingredient.

The distribution of bacteria isolated from nosocomial infection has been changed over time. According to a report of NNIS (National Nosocomial Infection Surveillance System), USA, Gram-positive bacteria particularly *Staphylococcus aureus* have been increasing in number among those isolated bacteria since late 1980s, and this phenomenon is consistent with that in Korea. According to a report made in Korea, the dominant distribution is *E. coli*, *Pseudomonas aeruginosa*, coagulase negative *Staphylococcus* and *Staphylococcus aureus* follow in that order. But, the isolation of *Staphylococcus aureus* is increasing gradually. Korean Society for Nosocomial Infection Control (KSNIC) reported in 1996 that *Staphylococcus aureus* took 17.2% of total isolated pathogenic microorganisms and *Pseudomonas aeruginosa* (13.8%) and *E. coli* (12.3%) followed. And, 78.8% of the total *Staphylococcus aureus* isolated were confirmed to have resistance against antibiotics.

Based on the above finding, the disinfectant containing the antimicrobial protein originated from the bacteriophage SAP-2 of the present invention that is able to kill specifically *Staphylococcus aureus* can be effectively used as a disinfectant specifically for hospitals and public health. It is also available as a general life disinfectant, a food and kitchen disinfectant, and a stall disinfectant. Moreover, the disinfectant of the invention does not use bacteriophage itself (microorganism), but use protein, which people can accept for food and cooking without aversion to it.

Advantageous Effect

As explained hereinbefore, the antimicrobial protein originated from the bacteriophage SAP-2 of the present invention can selectively kill *Staphylococcus aureus*, so that it can be widely used as a preventive and therapeutic agent for infectious disease caused by *Staphylococcus aureus*, as an antibiotic, as an antibacterial agent for cosmetics, as a natural antiseptic, and as a multi-purpose disinfectant.

DESCRIPTION OF DRAWINGS

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Isolation of *Staphylococcus aureus* and Bacteriophage Having Killing Activity Specific to *Staphylococcus Aureus*

<1-1> Isolation of *Staphylococcus Aureus*

Bacteriophages generally live together with bacteria in natural system. To isolate the bacteriophage specifically infecting *Staphylococcus aureus*, samples were collected from everywhere where the inventors expected *Staphylococcus aureus* lives. To investigate the samples where *Staphylococcus aureus* really exists, the Baird-Parker agar medium, a *Staphylococcus aureus* selection medium, was used.

Particularly, the present inventors selected bovine mastitis as a target disease to isolate *Staphylococcus aureus*, the target microorganism. Mastitis is one of the most representative diseases caused by *Staphylococcus aureus*. Samples were taken from milk of a dairy cow with mastitis and *Staphylococcus aureus* was isolated therefrom using the Baird-Parker agar medium, a *Staphylococcus aureus* selection medium. The isolated *Staphylococcus aureus* was identified as *Staphylococcus aureus* by biochemical analysis including Gram staining method, catalase test and analysis with Vitek of bioMeriuex. The results are shown in Table 1.

TABLE 1

| Vitek ID | 200000-0 (A1-18) catalase + Coagulase+ |
|---|---|
| Type | Gram positive identification card (GPI) |
| Condition | Final |
| Time | 5 hours |
| Organism | *Staphylococcus aureus* |

PB + BAC − OPT + HCS + 6NC + 10B + 40B − ESC − ARG − URE − TZR + NOV − DEX + LAC + MAN + RAF − SAL − SOR − SUC + TRE + ARA − PYR + PUL − INU − MEL − MLZ − CEL − RIB − XYL − CAT + BH/CO+

<1-2> Isolation of the *Staphylococcus Aureus* Specific Bacteriophage

To isolate the *Staphylococcus aureus* specific bacteriophage, samples expected to contain the bacteriophage were cultured together with *Staphylococcus aureus*. The culture broth was centrifuged, filtered and then cultured again with *Staphylococcus aureus*, the bait for the isolation of the bacteriophage, and then lysis of *Staphylococcus aureus* was investigated by plaque assay.

Figure 1:
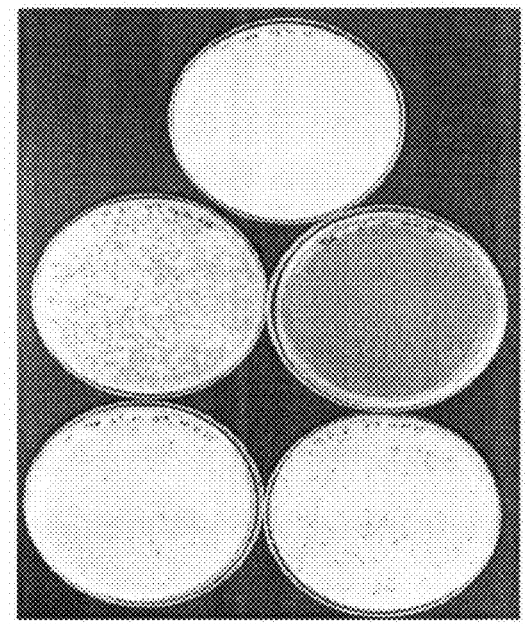
FIG. 1 is a photograph showing the result of plaque assay for detection of a bacteriophage specific to *Staphylococcus aureus*.
Figure 2:
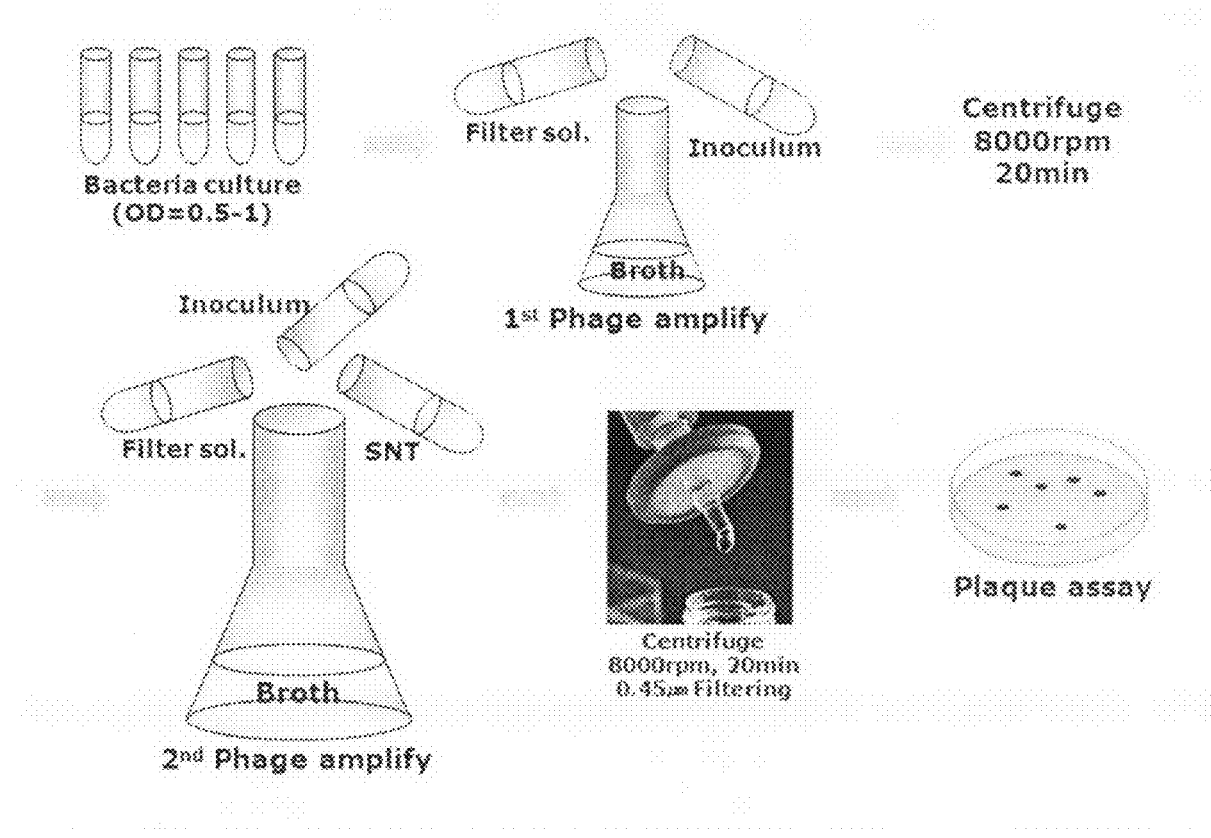
FIG. 2 is a schematic diagram illustrating the isolation procedure of the bacteriophage having killing activity specific to *Staphylococcus aureus*.

Particularly, to isolate the bacteriophage having killing activity specific to *Staphylococcus aureus*, samples were collected from soil and straw in a cowshed and sewage where the bacteriophage was expected to be. These samples were co-cultured with the previously isolated *Staphylococcus aureus* in example <1-1> at 37° C. for 3-4 hours. After cultivation, the culture broth was centrifuged for 20 minutes at 8,000 rpm. The supernatant was filtered with a 0.45 μm filter. With resultant filtrate, the *Staphylococcus aureus* specific bacteriophage was isolated by plaque assay (FIG. 1). The method used for isolation of the *Staphylococcus aureus* specific bacteriophage is shown in the schematic diagram of FIG. 2.

Figure 3:
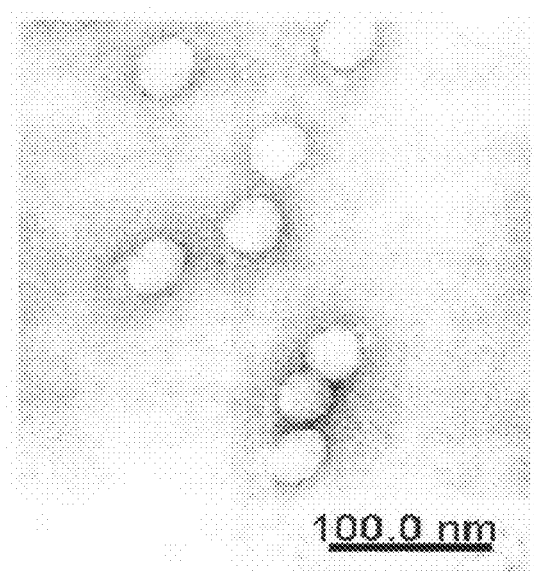
FIG. 3 is an electron microphotograph showing the *Staphylococcus aureus* specific bacteriophage isolated through plaque assay.

To observe the morphology of the obtained bacteriophage, CsCl density gradient (density: 1.15 g/ml, 1.45 g/ml, 1.50 g/ml and 1.70 g/ml) centrifugation (38,000 rpm, 22 hours, 4° C.) was performed, leading to the purification of the bacteriophage. The purified bacteriophage was loaded in a cupper grid, followed by negative staining with 2% uranyl acetate and drying. The morphology was observed under electron microscope. As a result, the isolated bacteriophage was confirmed to be the one belonging to φ29-like virus genus, Podoviridae family according to the morphological classification method (FIG. 3). The size of the bacteriophage was approximately 36.4 nm and named bacteriophage SAP-2.

EXAMPLE 2

Figure 4:
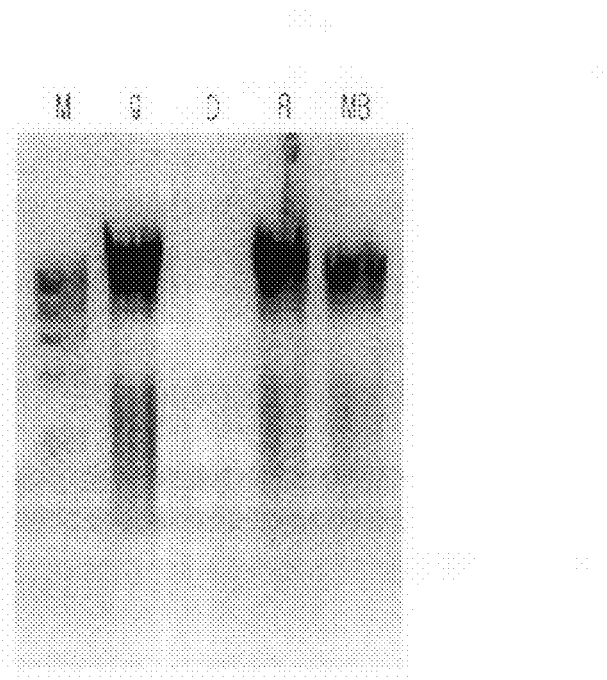
FIG. 4 is a photograph showing the characteristics of the genome extracted from bacteriophage. Lane g: genome treated with nothing; Lane D: genome treated with DNase; Lane R: genome treated with RNase A; Lane MB: genome treated with mung bean nuclease; and Lane M: molecular size marker.

Genetic Characteristics of the *Staphylococcus Aureus* Specific Bacteriophage SAP-2 Isolated The genome of the isolated bacteriophage SAP-2 was analyzed. To do so, the genome of the bacteriophage SAP-2 was first extracted by the conventional method and its genetic characteristics were examined. Particularly, 50 ml of *Staphylococcus aureus* culture broth ($OD_{600}=1$) and 1 ml of filtered bacteriophage suspension at the concentration of $1 \times 10^8$ pfu/ml were added into 200 ml of TSB (Tryptic Soy Broth) medium (casein digest, 17 g/l; soybean digest, 3 g/l; dextrose, 2.5 g/l; NaCl, 5 g/l; dipotassium phosphate, 2.5 g/l) in a 1 l flask, followed by shaking-culture at 37° C. for 34 hours. Then, lysis of *Staphylococcus aureus* was observed. After confirming lysis, the culture broth was filtered with a 0.45 μm filter. To eliminate DNA and RNA of *Staphylococcus aureus* remaining in the filtered culture broth, DNase and RNase (200 U each) were added to 10 ml of the filtered culture broth, which stood at 37° C. for 30 minutes. To inactivate the enzymes (DNase and RNase) therein, 500 ml of 0.5 M ethylenediaminetetraacetic acid (EDTA) was added thereto, which stood for 10 minutes. Next, to destroy outer wall of bacteriophage, 100 µl of proteinase K (20 mg/ml) and 500 µl of 10% sodium dodecyl sulfate (SDS) were added thereto, followed by incubation at 65° C. for 1 hour. After one hour incubation, 10 ml of phenol:chloroform:isoamylalcohol mixture (25:24:1) was added thereto and mixed well. The mixture was centrifuged at 18,000 rpm to separate layers. Upper layer was recovered, to which two times the volume of 100% cold alcohol was added, followed by extraction of pure genome. To investigate whether the genome extracted from bacteriophage was DNA or RNA, DNase I (10 U/µl) and RNase A (10 µg/µl) were added respectively, followed by incubation at 37° C. for 1 hour. The genome was also treated with mung bean nuclease (45 U/µl) for 15 minutes at room temperature to determine whether it was a single stranded DNA or a double-stranded DNA, in case it would be confirmed to be DNA. Electrophoresis was performed with those treated samples using 0.8% agarose gel and fragmentation pattern by each enzyme was investigated. As a result, the obtained genome was sensitive to DNase I (FIG. 4). The sensitivity to DNase I indicated that the genome was DNA and the non-sensitivity to mung bean nuclease indicated that the genome was a double stranded DNA. Therefore, it was confirmed that the genome of the bacteriophage was a double stranded DNA.

Figure 5:
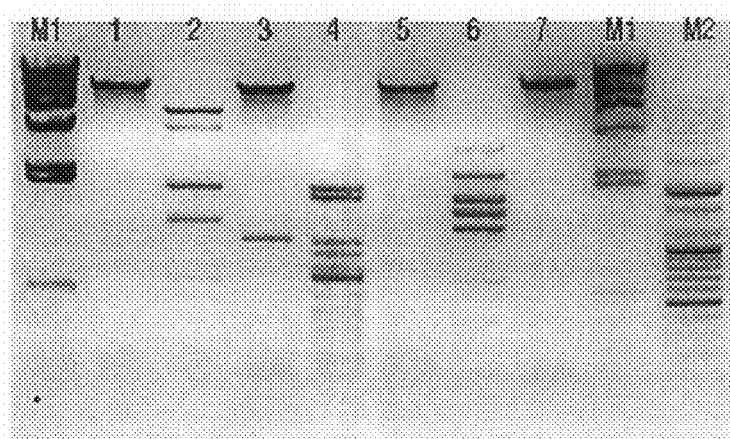
FIG. 5 is a photograph showing the digestion pattern of the genome extracted from bacteriophage by restriction enzymes. Lane M1: molecular size marker; Lane 1: digestion pattern by Sal; Lane 2: digestion pattern by Nde; Lane 3: digestion pattern by Mbo I; Lane 4: digestion pattern by Dra; Lane 5: digestion pattern by BamHI; Lane 6: digestion pattern by Acc I; Lane 7: gDNA of bacteriophage SAP-2; and Lane M2: molecular size marker.
Figure 6:
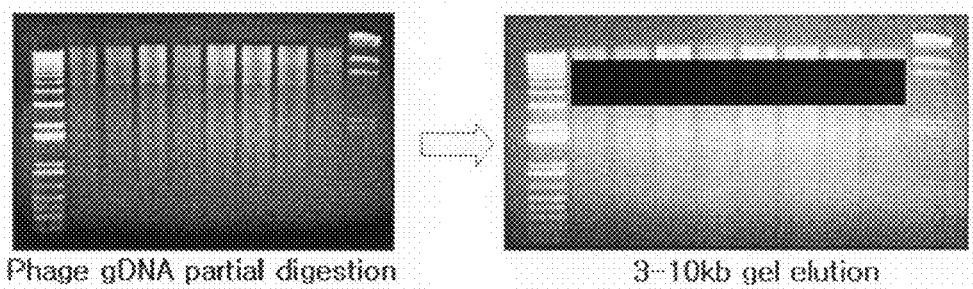
FIG. 6 is a schematic diagram illustrating the construction procedure of the genomic library of the bacteriophage.
Figure 6:
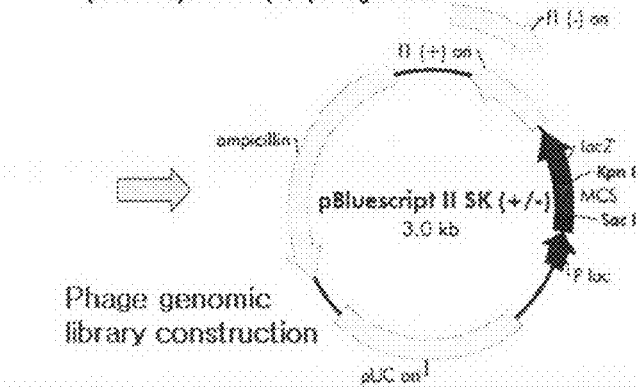
Figure 6:
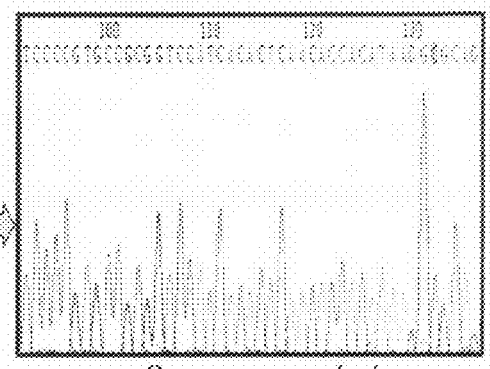

The genome extracted from the isolated bacteriophage was a genomic DNA (gDNA). To analyze the gene sequence of the gDNA, the genome was treated with different restriction enzymes and fragmentation patterns by different enzymes were observed (FIG. 5). Nde I was considered to be most appropriate for the construction of gDNA library. Thus, gDNA library was constructed by the conventional method using Nde I-treated DNA fragments. The method for the construction of gDNA library is shown in FIG. 6. Direct sequencing of gDNA of bacteriophage SAP-2 was performed to identify the whole nucleotide sequence of bacteriophage genome.

Particularly, DNA fragments were obtained by treating the gDNA of bacteriophage SAP-2 with Nde I according to the conventional method. Vector fragments were also prepared by treating the modified pGEM T-easy vector (Promega) with Nde I. The pGEM T-easy vector was the vector designed for TA-cloning. So, the vector could not be used as it was. Instead, T-overhang of the end of the vector was eliminated by the conventional method known to those in the art and then blunt-ended ligation was carried out, resulting in a circular modified vector. The DNA fragments and the vector fragments derived from the modified vector were ligated using T4 ligase. The resultant recombinant plasmid having the DNA fragment of bacteriophage SAP-2 was introduced into *E coli* Top 10F' via electroporation, a kind of electro-transformation. The transformant transformed with the recombinant plasmid was selected on the agar plate medium containing ampicillin supplemented with X-Gal (5-bromo-4-chloro-3-indolyl-beta-D-galactopyranoside) and isopropyl β-D-1-thiogalacto-pyranoside (IPTG) by using Blue-White colony selection. The selected single colony was inoculated into the medium containing ampicillin, followed by shaking-culture for overnight. Plasmids were extracted from the culture cells above using a plasmid purification kit (Intron). The extracted plasmids were electrophoresed using 0.8% agarose gel to confirm the size. Based on the size, recombinant plasmids were selected.

The numbers of selected plasmids were 3 in total and thus the numbers of clones obtained were also 3. The clones were cultured again and plasmids were extracted from the culture cells by the same manner as described above and the nucleotide sequences of the extracted plasmids were analyzed. Direct nucleotide sequencing of the gDNA of bacteriophage SAP-2 was also performed. Sequences of primers used herein are shown in Table 2.

TABLE 2

| Primer | Nucleotide sequence |
|---|---|
| T7 promoter | TAATACGACTCACTATAGGGCGA |
| SP6 promoter | GTATTCTATAGTGTCACCTAAAT |
| 1 | CGTAATGCTTCAAAATGTTC |
| 2 | GAGCAATGTTAGTTGATTACTCATT |
| 3 | CCATTTAAAAAATAATCATCACGTT |
| 4 | TGCAATTCATATATTAGATGATAA |
| 5 | TATGCTTTATATGGAGGTTGATAAC |
| 6 | AATTAGTGTACCGTCACCTAAAGA |
| 7 | TGCAACACCATCGTGATGTA |
| 8 | GTTGTTGAACATCGCAACAG |
| 9 | CAAAATCTGATAAAAACGTCAT |
| 10 | GACGTGATGAGGATTATTAT |
| 11 | ATAAATTCTCTTTCTTTTTCCTCAAATTCAAATCTCGCTAATGT |
| 12 | CATACGTGGATAATTACGTTTCAACATTAATTCCTCATTT |
| 13 | ATCAAATTCATTTAAAATTTTCTTTCT |
| 14 | AATGTCACCTATGTTTAATGCAGA |
| 15 | AGTTCATCATTTAAGAATTGAACAACAGAACT |
| 16 | TTTGTTGCTCTAATGATGTAATACGTTGTTCTAATATAACAG |
| 17 | TCACTTGCAATAATACCACTTTCTAAT |
| 18 | GTCAAGTATCATTTTAATACAATTT |
| 19 | TCATTATACATTACGTGACGCTTA |
| 20 | AGCTTCTCTTTCTTTTTTCCATCTA |
| 21 | GAACTTCATTGTATTTAGCGCTGTTG |
| 22 | TGAATCTTCATATGGTCGACCTGCAG |
| 23 | ATTTAATAGTTTTGCACAAGTACCAA |
| 24 | CAAACTAACCCATCTGATAAACAAAC |
| 25 | AACCTAATGGCTATTGGTTCCAACCA |
| 26 | GGTAACAGTTCAGTTAATTCACAT |
| 27 | GGTGCCATAATTTATTATTCCTCC |
| 28 | TTAATCGTACCTAATTTAATATCAC |
| 29 | AACGTAAATCGTTATTACTTGCAATG |
| 30 | CGTTACAACACCCGGAGAATATTA |

TABLE 2-continued

| Primer | Nucleotide sequence |
|---|---|
| 31 | CCAAATGTCCAAGATTTTGAATAA |
| 32 | TTTAAAATGTACAGGTACGTATAC |
| 33 | TTGAATTTAACGAATATAATTTGGC |
| 34 | ATATTATCATGATTGCACATAACTG |
| 35 | GTAAAAGGTTATGGACGTTTTAAT |
| 36 | AATTTTTATGACTATATAAAATCATT |
| 37 | ACAAAAAACATTTAACAACACGTAT |
| 38 | AAATAAAATACAAAACATAATCAAT |

The nucleotide sequence of the total genome of the bacteriophage SAP-2 obtained by the above two methods was represented by SEQ. ID. NO: 1. The total number of nucleotides forming the genome of bacteriophage SAP-2 was 17938.

Homology of the said bacteriophage genome with the collected sequence records of bacteriophage genomes was investigated by BLAST (http://www.ncbi.nlm.nih.gov/BLAST/) on Web, referring to analyzed and reported bacteriophage nucleotide sequence. As a result, the nucleotide sequence of the genome of bacteriophage SAP-2 showed 86.0% homology with *Staphylococcus aureus* phage phi P68, 81.8% with 44AHJD and 49.2% with bacteriophage 66. These three bacteriophages were all bacteriolytic Podoviridae bacteriophages specifically infecting *Staphylococcus aureus*. The size of phi P68 genome is 18,227 bp, the size of 44AHJD genome is 16,784 bp and the size of bacteriohphage 66 genome is 18,119 bp. To understand genetic functions of each gene, open reading frame (ORF) was analyzed by NCBI ORF finder (http://www.ncbi.nlm.nih.gov/gorf/gorf.html) and Vector NTI ContigExpress (INFORMAX) program, based on the gene sequence of phi P68. Referring to the paper published in FEMS Microbiology Letters (Complete nucleotide sequence and molecular characterization of two lytic *Staphylococcus aureus* phages: 44AHJD and P68, 2003, 219: 275-283), ORF homology was compared. The results are shown in Table 3.

TABLE 3

| ORF | Frame | Start | End | Putative translation initiation sites | No. of amino acids | Size (Da) | PI | Putative function |
|---|---|---|---|---|---|---|---|---|
| 1 | +1 | 343 | 645 | caaaacaaggaggt aacaaa | 100 | 11550.89 | 3.9169 | Unknown |
| 2 | +3 | 660 | 896 | ttagaaaggaatgat ataat | 78 | 9306.71 | 6.2418 | Unknown |
| 3 | +3 | 900 | 1268 | aattaaagaggaga aataaa | 122 | 14292.12 | 5.301 | single stranded DNA binding protein |
| 4 | +1 | 1318 | 1497 | attttatgaggtgcta aaca | 59 | 7141.18 | 7.4913 | Unknown |
| 5 | +3 | 1500 | 1913 | ttaaggagatataaa aatg | 137 | 16088.36 | 4.7637 | Unknown |
| 6 | +1 | 1906 | 2073 | atacgggaaagtaat agacc | 55 | 6369.95 | 6.3126 | Unknown |
| 7 | +1 | 2101 | 2559 | gctttatatggaggtt gata | 152 | 18423.76 | 9.9897 | Unknown |
| 8 | +3 | 2718 | 3854 | caaatagaattagttg atga | 378 | 45857.7 | 5.9219 | Encapsidation protein |
| 9 | +3 | 3888 | 6157 | aagattatgggattac ttga | 761 | 90383.05 | 5.4283 | DNA polymerase |
| 10 | -2 | 7706 | 6270 | acgattctgaaaaga gtgat | 478 | 52080.48 | 9.4347 | Unknown |
| 11 | -1 | 8020 | 7991 | agagaggggtata aaa | 140 | 16345.35 | 8.1902 | Holin |
| 12 | -2 | 9869 | 8106 | ctattttta tggaggtaaa a | 587 | 68346.17 | 6.2139 | Tail protein |
| 13 | -1 | 11371 | 10838 | taaataagaggtgta aaca | 177 | 20359.5 | 5.3719 | Unknown |
| 14 | -2 | 12185 | 11436 | acataaaaaatagga gtgtt | 249 | 28653.85 | 6.8931 | Amidase |
| 15 | -3 | 14159 | 14140 | tggtaaaggtggaaa attat | 647 | 74574.47 | 5.5835 | Minor structural protein |
| 16 | -2 | 13910 | 14154 | agatgaaagtagtga tttaa | 259 | 30037.53 | 5.2211 | lower collar protein |

TABLE 3-continued

| ORF | Frame | Start | End | Putative translation initiation sites | No. of amino acids | Size (Da) | PI | Putative function |
|---|---|---|---|---|---|---|---|---|
| 17 | -1 | 15652 | 14903 | ttaatgtagtggttggtgaa | 249 | 28571.06 | 4.3332 | upper collar protein |
| 18 | -3 | 17126 | 15900 | acgtagaggaggaataataa | 408 | 46804.98 | 5.5568 | major head protein |
| 19 | -3 | 17315 | 17133 | atttagattaggaggaaaat | 60 | 6955.51 | 4.1365 | Unknown |
| 20 | -3 | 17663 | 17325 | atattttggaggtgtcacaa | 112 | 12991.9 | 3.6313 | Unknown |

EXAMPLE 3

Cloning of the Gene Encoding the Lytic Protein and Construction of Expression Plasmid From the gene sequencing and ORF analysis performed in Example 2, the present inventors identified ORF of amidase which seemed to be much likely lytic protein. Domain of amidase gene was thoroughly examined. As a result, CHAP (cysteine, histidine-dependent amidohydrolases/peptidases) region and SH3_5 region were analyzed. CHAP region is the region frequently found in peptidoglycan amidase that plays a role in cell lysis by breaking peptidoglycan layer of bacteria, which has L-muramoyl-L-alanine amidase activity and D-alanyl-glycyl endopeptidase activity. SH3_5 region is the cell wall targeting domain which binds to a specific region of bacterial cell wall to make the lytic protein break peptidoglycan layer fast and easy.

The gene encoding the lytic protein in bacteriophage SAP-2 genome is 750 bp and the lytic protein expressed thereby is composed of 250 amino acids. The gene encoding the lytic protein is represented by SEQ. ID. NO: 2 and the lytic protein has the amino acid sequence represented by SEQ. ID. NO: 3.

The present inventors constructed an expression plasmid for the expression of the said lytic protein. The gene corresponding to amidase was cloned into pBAD-TOPO vector (Invitrogen) by using Nco I and Not I restriction enzyme sites. First, enterokinase cleavage site in pBAD-TOPO vector was eliminated before cloning, in which Not I restriction enzyme site was inserted, followed by cloning. The constructed expression plasmid for the expression of the said lytic protein is named pBAD::lysinM. E. coli Origami (DE3) (Novagen) was transformed with the expression plasmid, leading to the construction of the production host of lytic protein. The constructed production host was deposited at Biological Resource Center, Korea Research Institute of Bioscience and Biotechnology on Jul. 18, 2007 (Accession No: KCTC 11152BP).

EXAMPLE 4

Over-Expression of Antimicrobial Protein

The antimicrobial protein was over-expressed using the E. coli transformant constructed in Example 3. The expression system based on pBAD-TOPO vector is the L-arabinose-mediated induction system, which is favorable in the expression of toxic protein (referred to the instruction of the manufacturer under the title of "pBAD expression system" and the instruction 25-0257 published in 2004).

Figure 7:
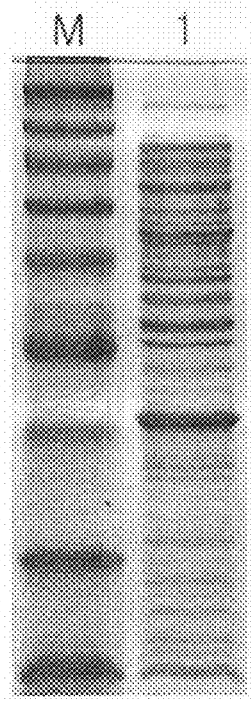
FIG. 7 is a photograph showing the result of protein electrophoresis with the expressed antimicrobial protein. Lane M: protein size marker (198, 115, 90.5, 61.5, 46.2, 37.8, 26, 18.5, and 9 kDa, from the top); and Lanes 1: cell lysate containing expressed antimicrobial protein. '*' indicates the location of over-expressed antimicrobial protein.

The over-expression inducing process is described in detail hereinafter. The constructed plasmid contains ampicillin resistant gene and the production host itself has tetracyclin resistant gene. So, the production host of lytic protein is inoculated in 5 ml of LB medium (trypton, 10 g/L; yeast extract, 5 g/L; NaCl, 10 g/L) containing ampicillin and tetracyclin, followed by shaking-culture at 37° C. for overnight. 100 µl of the culture broth was re-inoculated in 10 ml of fresh LB medium containing ampicillin and tetracyclin, followed by shaking-culture at 37° C. When $OD_{600}$ of the culture broth reached 0.5, L-arabinose was added (final conc.: 0.2%) thereto to induce the expression of the antimicrobial protein. Then, the culture temperature was adjusted to 23° C., followed by low temperature culture for 12 hours. Then, 1 ml of the cell culture broth was taken and centrifuged at 8,000 rpm for 5 minutes to obtain cell pellet. The cells were lysed by resuspending of the cell pellet in 100 µl of 1% SDS solution. 12 µl of the cell lysate was taken for electrophoresis. 3 µl of 5× sample loading buffer was added to the cell lysate and mixed well. The gel loading sample was boiled for 5 minutes. Electrophoresis was performed with the sample by the conventional method to confirm over-expression of the antimicrobial protein. The results are shown in FIG. 7.

EXAMPLE 5

Lytic Activity of the Expressed Antimicrobial Protein

To investigate lytic activity of the expressed antimicrobial protein, 100 ml of the culture broth of the E. coli transformant (KCTC 11152BP) was centrifuged at 8,000 rpm for 5 minutes and the resultant cell pellet was recovered. The cells were resuspended in 1 ml of 80 mM Tris-HCl (pH 4.0) buffer. The cells in this cell suspension were disrupted by sonication as follows; sonication was performed for 20 seconds to disrupt cells and stopped to take a break for 5 seconds, which was repeated for 20 minutes. The obtained whole cell lysate was centrifuged again (10,000×g, 5 minutes) to obtain supernatant. Using the supernatant, antimicrobial activity of the expressed antimicrobial protein was examined. The bacteria used for the investigation of lytic activity were three kinds of Staphylococcus aureus, clinically isolated from milk of daily cattle of farms in Gyunggi-do and Gangwon-do, Korea by the present inventors.

Figure 8:
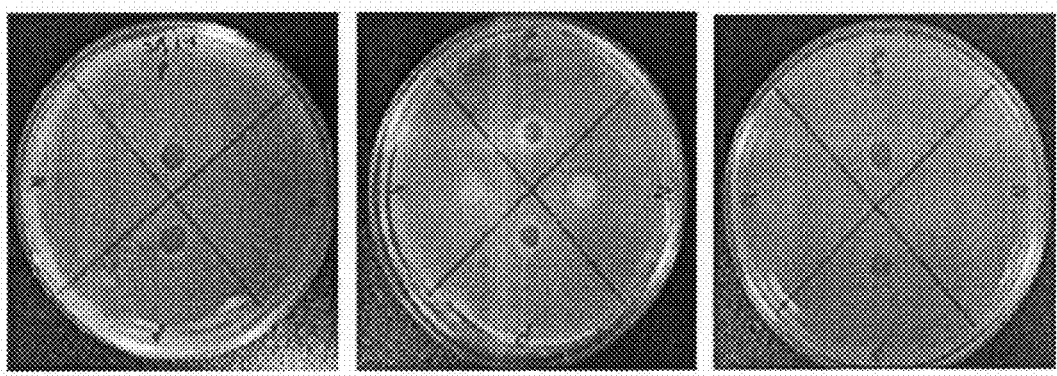
FIG. 8 is a set of photographs showing the results of the investigation of lytic activity against three strains of *Staphylococcus aureus* clinically isolated. *Staphylococcus aureus* used for the above three experiments was all different kinds and the clear plaque was generated by bacteriolytic activity of the lytic protein of the present invention.

1 ml of Staphylococcus aureus culture broth ($OD_{600}$=1 in TSA medium) was spread on agar plate and dried. 5 µl of the supernatant obtained after centrifugation of the cell lysate was dropped onto the dried medium above, followed by incubation in a 37° C. incubator for overnight. Then, the lytic activity was investigated. As shown in FIG. 8, transparent plaque was observed, indicating bacteriolytic activity of the said antimicrobial protein.

Figures 9, 10:
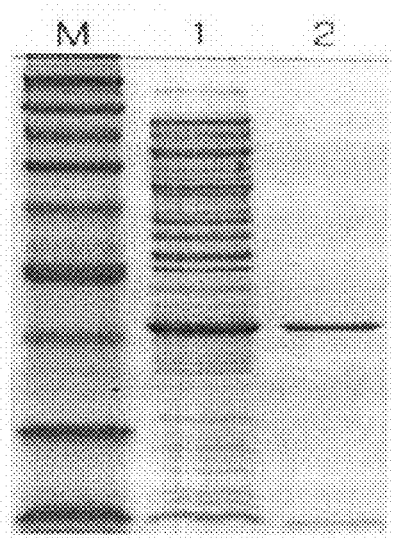
FIG. 9 illustrates the bacteriolytic activity of each lytic protein against *Staphylococcus aureus*, more precisely against 5 kinds of *Staphylococcus aureus* isolated from dairy cows with mastitis and 3 kinds of *Staphylococcus aureus* isolated from human. Phage: treated with bacteriophage SAP-2; and Lysin: treated with the bacteriophage SAP-2 originated antimicrobial protein.
FIG. 10 is an electrophoresis photograph illustrating the purified antimicrobial protein. Lane M: protein size marker (from the top, 198, 115, 90.5, 61.5, 46.2, 37.8, 26, 18.5, and 9 kDa); Lane 1: lysate before purification; and Lane 2: protein sample after purification. The dark stained band indicates the location of the over-expressed antimicrobial protein.

Bacteriolytic activity of the antimicrobial protein was compared with that of bacteriophage SAP-2, the mother bacteriophage of the antimicrobial protein above. Each bacterium was cultured by the same manner as described above, which was spread on plate medium, to which 5 μl of bacteriophage SAP-2 suspension and the antimicrobial protein solution (supernatant obtained from centrifugation using cell lysate in earlier experiment), followed by culture at 37° C. for overnight. Then, bacteriolytic activity of the bacteriophage and the protein was investigated. The results are shown in FIG. 9. In this experiment, 5 kinds of *Staphylococcus aureus* isolated from cow and 3 kinds of *Staphylococcus aureus* isolated from human were used. As a result, the spectrum of bacteriolytic activity of the lytic protein was broader than that of the bacteriophage itself. Therefore, the antimicrobial protein of the present invention was confirmed to have broader spectrum of bacteriolytic activity than the bacteriophage itself.

EXAMPLE 6

Separation and Purification of the Expressed Antimicrobial Protein 500 ml of the culture broth of the transformant (KCTC 11152BP) cultivated in LB medium was centrifuged at 8,000 rpm for 5 minutes to obtain cell precipitate. The precipitate was suspended in 6 ml of 80 mM Tris-HCl buffer (pH 4.0). The cells in the suspension were disrupted by sonication by the same manner as described in Example 5. The cell lysate was centrifuged at 8,000 for 5 minutes to remove cell debris. Ammonium sulfate precipitation (30% (w/v)) was performed with the resultant supernatant to concentrate the expressed antimicrobial protein. More precisely, ammonium sulfate was added at the final concentration of 30% (w/v) and the resultant solution was left in ice for 15 minutes to precipitate the expressed protein. 15 minutes later, the solution was centrifuged at 10,000×g for 15 minutes to recover the precipitate. The precipitate was dissolved in 2 ml of adsorption buffer (25 mM sodium phosphate, pH 5.8) for chromatography. To remove the excessive ammonium sulfate, the prepared protein solution was dialyzed against adsorption buffer at 4° C. for overnight by replacing the adsorption buffer with a fresh buffer from time to time. Upon completion of dialysis, the protein solution was centrifuged at 10,000×g for 25 minutes to remove insoluble substances. The protein solution was then filtered with 0.2 μm filter, followed by cation-exchange chromatography. At that time, HiTrap SPFF (GE Healthcare) was used as the cation-exchange resin. The column was equilibrated with the adsorption buffer before sample loading. Then, the sample containing the antimicrobial protein was loaded onto the column, followed by washing with 100 ml of the adsorption buffer. In this condition, other proteins originated from *E. coli* did not adhere to the matrix of column. The antimicrobial protein was eluted by using 25 mM of sodium phosphate solution (pH 5.8) containing potassium chloride at different concentrations from 0.2 to 0.8 M. To remove potassium chloride used for the elution of the antimicrobial protein, the eluent fraction containing the antimicrobial protein was dialyzed against 25 mM of sodium phosphate solution (pH 5.8) at 4° C. for overnight by replacing the sodium phosphate solution with fresh sodium phosphate solution from time to time. The dialysate was concentrated through performing dialysis of protein solution against polyethyleneglycol 20,000. The results are shown in FIG. 10.

EXAMPLE 7

An Example of the Application of the *Staphylococcus Aureus* Specific Antimicrobial Protein for the Prevention of Infectious Disease Caused by *Staphylococcus Aureus*

100 μl of the supernatant obtained from centrifugation of the cell lysate containing the antimicrobial protein prepared in Example 5 was added into a 9 ml of nutrient broth (beef extract 3 g/l, peptone 5 g/l). 100 μl of the purified antimicrobial protein prepared in Example 6 was added into another 9 ml of nutrient broth. A control medium was prepared without addition of the supernatant containing the antimicrobial protein and the purified antimicrobial protein. *Staphylococcus aureus* suspension was added into each medium at a starting optical density at 600 nm ($OD_{600}$) of 0.5, followed by investigation of the growth of *Staphylococcus aureus*. As shown in Table 4, in the medium not treated with the supernatant containing the antimicrobial protein and the purified antimicrobial protein, *Staphylococcus aureus* was growing so well (30 minutes later: $OD_{600}$=0.8). On the other hand, in the mediums treated with the supernatant containing the antimicrobial protein or the purified antimicrobial protein, *Staphylococcus aureus* was not grown at all (10 minutes later: $OD_{600}$=0.1, 60 minutes later: $OD_{600}$=0.05). From the above results, it was confirmed that the supernatant obtained from centrifugation of the cell lysate prepared in Example 5 or the purified antimicrobial protein prepared in Example 6 was very effective in the prevention of the infection of *Staphylococcus aureus*.

TABLE 4

| *Staphylococcus aureus* killing activity ($OD_{600}$) | | | |
|---|---|---|---|
| | Starting optical density | 10 minutes of culture | 60 minutes of culture |
| Control (non-treated) | 0.5 | 0.6 | 0.8 |
| Experimental group 1 (Example 5) | 0.5 | 0.12 | 0.08 |
| Experimental group 2 (Example 6) | 0.5 | 0.1 | 0.05 |

EXAMPLE 8

An Example of the Application of the *Staphylococcus Aureus* Specific Antimicrobial Protein for the Treatment of Infectious Disease Caused by *Staphylococcus Aureus*

15 dairy cows with mastitis caused by *Staphylococcus aureus* were selected to investigate the effect of the antimicrobial protein obtained in Example 6 on the treatment of mastitis. The cows were divided into three groups (5 cows per group). 10 ml of the antimicrobial protein solution prepared by diluting (100×) the concentrate of Example 6 with 50 mM sodium phosphate solution (pH 6.5) was sprayed on the lesion of dairy cows of first group every day and 10 ml of 50 mM sodium phosphate solution (pH 6.5) without the antimicrobial protein was sprayed on the second group every day with same manner, particularly on the infected regions. In addition, 10 ml of PBS was sprayed on the third group every day with same manner. The spray was continued for 10 days. After 10 days of such treatment, the population of *Staphylococcus aureus* in the milk obtained from the cows with mastitis was investigated. As shown in Table 5, significant treatment effect was observed in the group sprayed with the antimicrobial protein solution. From the result, it was confirmed that the antimicrobial protein obtained in Example 6 was very effective in the treatment of infectious disease caused by *Staphylococcus aureus*.

TABLE 5

Treatment effect on disease caused by *Staphylococcus aureus* infection (number of *Staphylococcus aureus*)

| | Before treatment | After treatment |
|---|---|---|
| Control (PBS) | $1.6 \times 10^4$ cfu/ml | $1.7 \times 10^4$ cfu/ml |
| Experimental group (100X diluted antimicrobial protein concentrate of Example 6) | $1.7 \times 10^4$ cfu/ml | $1.3 \times 10^2$ cfu/ml |

TABLE 5-continued

Treatment effect on disease caused by *Staphylococcus aureus* infection (number of *Staphylococcus aureus*)

| | Before treatment | After treatment |
|---|---|---|
| Comparative group (sodium phosphate solution) | $1.5 \times 10^4$ cfu/ml | $1.6 \times 10^4$ cfu/ml |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated antimicrobial protein having killing activity specific to *Staphylococcus aureus* comprising the amino acid sequence represented by SEQ. ID. NO: 3.

2. The isolated antimicrobial protein according to claim 1, wherein the antimicrobial protein is originated from the Podoviridae bacteriophage (Accession No: KCTC 11154BP).

3. A pharmaceutical composition for the treatment of a disease caused by *Staphylococcus aureus*, containing the antimicrobial protein of claim 1 as an active ingredient.

4. A pharmaceutical composition for the treatment of a disease caused by *Staphylococcus aureus*, containing the antimicrobial protein of claim 2 as an active ingredient.

5. The pharmaceutical composition according to claim 3, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

6. The pharmaceutical composition according to claim 4, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

7. An antibiotic composition containing the antimicrobial protein of claim 1 as an active ingredient.

8. An antibiotic composition containing the antimicrobial protein of claim 2 as an active ingredient.

9. A disinfectant containing the antimicrobial protein of claim 1 as an active ingredient.

10. A disinfectant containing the antimicrobial protein of claim 2 as an active ingredient.

* * * * *

SEQUENCE LISTING

```
<160> NUMBER OF SEQ ID NOS: 3

<210> SEQ ID NO 1
<211> LENGTH: 17938
<212> TYPE: DNA
<213> ORGANISM: Podoviridae bacteriophage

<400> SEQUENCE: 1
taaatataat cggaaaaagt ttttgtaaat ttacacctcc ccaccgttta aaataaacga        60
ttatacaaat caaaacttat aaattaactt atcatttcta aactaaactt ataaaaaatg       120
ttcacctact ttcccaactt atctaaccta ttacatattc attaattaca aaatatatac       180
atctattgac ttttatccaa aattatgatt tgaaattaaa atctagtttc ttctattaaa       240
tagtagtttt aaattattta aactttttta cgatattttta ttgacaaaac atttaaacat       300
ttgctatact aagtatgtaa tcaaaacaag gaggtaacaa aaatgattaa tgttgataat       360
gcaccatcag aaaaaggtca agcatatact gaaatgttgc aattattcaa taaactgatt       420
caatggaatc cagcatatac gtttgataac gcaattaact tagtatctgc ttgtcaacaa       480
ctattattaa actataacag ttctgttgtt caattcttaa atgatgaact caacaacgaa       540
actaagccag aatctatttt agcttatatt gctggtgacg atgcaatcga acagtggaat       600
atgcacaaag gttttttatga aacgtataat gtttacgtat tttagaaagg aatgatataa       660
tgaaagctga tgacattata actttacgtg ttaaaggtta tatattccat tacttagatg       720
aatcaaatga atacattgaa gaatttatac cacttcacga gtatcattta actaaaacac       780
aagcaataga attattacct aacacatgta cactattatc aactacacgc aaaacgaaaa       840
aaatccaagt atattacaat gatttactac aaatttcaat taaagaggag aaataaaaaa       900
tgacaaacgt aaaagaaatt ttatcaagac accaaaatac aacagcgaga tttgaatttg       960
aggaaaaaga aagagaattt ataaaactat cagaattagt tgaaaaatac ggtattaaaa      1020
aagagtatat cgttagagca ttattcacaa acaaagaatc aaaattcggt gtacagggtg      1080
ttatcgtcac tgacgactat aatgtaaact taccgaacca cttaacagag ttaattaaag      1140
aaatgagatc agacgaggac gttgttaaca ttatcaatgc tggtgaagtg caatttacaa      1200
tttatgaata tgaaaacaaa aaaggtcaaa aaggttactc aatcaacttt ggtcaagtat      1260
cattttaata caatttcata ggggatattt atccccatt ttatgaggtg ctaaacaatg      1320
gaaaaaatat acactgccgt attattatac aatgtatcaa ttaatgaaac atatgaacat      1380
```

```
gaaattgaac aattcgaaaa aataaataaa gttaaggtaa tatatagtta ttttgacgca    1440
aacttttaca aaaaaggtgc atataatttt ggtgtaaaat acattaagga gatataaaaa    1500
tgaatattac aacaacatta aacacaaaaa aattaattaa ttatatttta gataatagag    1560
attgttttat gaataaaata acaaaattta catcactaag tggaaaatgt gttgttttg     1620 ttagatacgg tgaaatttct attgaatact atgatagtga tacaaaaaac aataatgatt    1680
tatttacttt agacattgac gttgatatta ataaacatgt ctttaattgt cttaaagttt    1740
attatataga acatacagaa gatataaaca taatatataa aaaggtgta tacatggggt     1800 gtactattga tgatgtatta tcatattttg aaaaaccatt agaaagtgat attactatta    1860
tttaccaagg caaagttatt tatgaatacg ggaaagtaat agaccatgaa taacctacta    1920
gatattatta ttgttttcct tttagcattt ttaattacac ttgtaatact tatgacaatg    1980
tatatacgtg tgtcatttgg tgttttattt actacattta ttatattcta cattatcttt    2040
ttattggttg tatatgcttt atatggaggt tgataacatt ggtttagaca tacgtctgaa    2100
atggatagat ggaaaaaaga aagagaagct agaaagaaa gagaagaaaa aaaatataaa      2160
aatgatttta gcggtatcaa ttttaaattt gacgataaag atttacaaga ggcttatatt    2220
gacgcatgga aacatttttc acatttacca catttaccaa agaaaaaaaa tgtatctcat    2280
gcaaacgctg tttcattagt tcgtggtaaa cgacataaaa aattaaatca tatactagaa    2340
atatataacc gtaatgataa taataacaaa aatgcaaaaa tgcataaata tgcattatat    2400
aatttacacg ccgaaaaaaa taaatcttca cttacaaaat atattaaaga aattgataac    2460 ttatttttg aaataggaaa atcagataga ccaaaaacaa caatagatga tatcaatgtt      2520
aggtataact ttttatatta tgcaacattt gaagaataac tttaatactg taaatgacat    2580
tataaactat tacaaggagc aaaaacatgg tgaaacaaaa tcgtttagac atggtaagag    2640
attatcaaaa tgcggtcaat catgtaagga aaaaaatacc agaaaactat aatcaaaatag    2700 aattagttga tgaactcatg aatgatgata tagactatta tatatctatt tcaaaccgtt    2760
ctgacggaaa atcgttcaac tatgtttcat ttttttattta tttagctatt aaacttgata    2820
taaaatttac tttattatca cgtcattata cattacgtga cgcttaccgt gattttattg    2880
aggaaatcat agataaaaac ccactattca aatctaagcg tgtcactttc agaagcgcta    2940
gagattattt agctattatc tatcaagata aagaaattgg cgtgattaca gatttgaata    3000
gcgctactga tttaaaatat cattctaact ttttaaaaca ctaccctatt attatatatg    3060
atgaattctt agcgcttgaa gatgactatt taattgatga gtgggacaag ttaaaaacaa    3120
tttatgaatc aatcgaccgt aaccatggta atgttgatta tattggtttt cctaaaatgt    3180
ttttactagg taatgctgtc aactttcaa gtcctatatt atccaattta aatatttata     3240
atttattaca aaaacataaa atgaatacat caagacttta caaaaacatt ttttttagaaa   3300 tgcgtcgaaa cgattacgtc aatgagaggc gtaatacacg tgcgtttaat tcaaatgatg    3360
acgctatgac aactggcgag tttgaattta acgaatataa tttggcagat gataatttaa    3420
gaaatcatat caaccaaaac ggtgattttt tctatattaa aactgacgat aaatatataa    3480
aaattatgta taatgttgat acattttaatg ctaacatcat tgtaataacct tatacaaaac   3540 aatatgagtt ttgcactaaa atcaaagata tcgatgacaa tgttatttat ctaagagaag    3600
atatgtttta taagaaaaac atggaacgat attactacaa tccaagtaat ttacattttg    3660
acaatgctta ttcaaaaaat tacgtggttg ataatgatag atatttatat ttagatatga    3720
ataaaattat aaaatttcat ataaaaaatg aaatgaagaa aaatattaac gaatttgaaa    3780
```

```
gaaaagaaaa gatatacgaa gataactata tagaaaatac aaagaagtat ttaatgaaac    3840
aatacggctt ataaaaggtg tgtaagatta tgggattact tgagtgtatg caatatcata    3900
aaaatcaacg taaaatgata ttgtactggg atattgaaac attatcgtac aataaaataa    3960
acggacgcaa taaaccaaca ttatataaaa acgtaacgta ttctgttgcg attggttggt    4020
ataatggtta cgaaattgat gttgaagtat tccccagttt tgaagccttt tatgatgatt    4080
ttttcaagta tgtttatcgc cgggatacaa tcacaaaatc aaaaacaaat attatcatga    4140
ttgcacataa ctgtaataaa tacgataatc attttttact taaagacacc atgcgttatt    4200
ttgataatat tacacgcgaa aatgtatatt taaaatctgc agaagaaaat gaacatacaa    4260
taaaaattca agaggctact attttagcca aaaatcaaaa tgtgatttta gaaaaacgtg    4320
ttaaatcttc aatcaattta gatttaacga tgtttttaaa tggttttaaa tttaatatca    4380
ttgataactt tatgaaaacc aatacatcaa tagcaacatt aggaaaaaag ctacttgacg    4440
ggggttattt aacagaaaac caacttaaaa cagattttaa ttatacaatt tttgataaag    4500
ataacgatat gtcagatagt gaagcttatg actatgctgt taagtgtttt gataatctta    4560
catctgaaca attaacctac attcataatg acgtgattat attaggtatg tgccatattc    4620
attatagtga cattttttcca aattttgact ataacaaatt aacattctca ctaaatatca    4680
tggaatctta tttgaataat gaaatgactc gttttcagtt actcaatcaa tatcaagata    4740
ttaaaatatc ttatacacat tatcattttc atgatatgaa ttttatgac tatataaaat    4800 cattttatcg tggtggttta aatatgtata ataccaaata tatcaataaa cttattgatg    4860
aaccttgttt ttctatagac atcaattcga gttatcctta cgtgatgtat catgagaaaa    4920
ttccaacatg gttatacttt tatgagcatt actcaaaacc aacattaatc cctactttt    4980 tagatgatga taattatttt tcattatata agattgataa agaggtattt aacgatgagg    5040
tattaattaa aatcaaatca cgcgtactac gtcagatgat tgttaaatac tacaataatg    5100
ataacgatta cgttaatatc aatacaaaca cattaagaat gatacaagac attacgggta    5160
ttgattgcac gcatatacgt gttaattcgt ttgttgtata tgaatgtgaa actttcacg    5220 cacgagatat tatatttcaa aactatttta ttaaaacaca aggtaaatta agaataaaa    5280 tcaatatgac aacacttac gactatcaca ttacagatga attaacgaa cacccctact    5340 caaatgaaga agtatgtta tcaaaagtcg ttttaaatgg tttatatggt atacctgctt    5400
tacgttcaca ctttaattta tttcgtttag atgaaaacaa cgaattgtat aacatcatta    5460
acggatacaa aaacacggaa cgtaaatttt tattctctac atttgtcaca tcacgttcat    5520
tgtataactt attagtacct ttccaatact taacggaaag tgaaattgac gacaattta    5580 tttattgcga cactgatagt ttgtatatga atcagttgt aaagccctta ttgaccccca    5640
gtttattcga ccctatatca ttaggcaaat gggatattga aaacgaacag atagataaga    5700
tgtttgtact gaatcataaa aaatatgctt atgaagtgaa tggaaagatt aaaattgcgt    5760
ctgctggtat accgaaaaac gccaaaaata caagcgtcga ttttgaaacc tttgtacgtg    5820
aacaattttt tgacggtgca attatagaaa acaataaaag tatctataat aatcaaggta    5880
cgatatcaat ttatccgtca aaaacagaaa ttgtttgtgg taatgtatat gatgaatatt    5940
ttactgatga acttaattta aaacgtgaat ttatcttaaa agacgctaga gaaaatttg    6000 accatagtca atttgatgat attctttata ttgaaagtga tattggttca ttttcactca    6060
atgacttatt tccatttgaa cgttcagtac ataacaaatc tgatttgcat atattaaaac    6120
aacaacatga tgacatcaaa aaaggcaact gttaaaataa cagtcgcctt ttctttgaga    6180
```

```
taacatgaaa aatgtgtacg aaaattgatt atgttttgta ttttatttac tagcattact    6240
agcatgtgtt cattatagca taaatcttta tgcaatacca ctaaagaata caatattatc    6300
acctgcgttt tctggtacac cgttaatgag tgtatacaat aatacacgtg acggtgcaac    6360
gtatggtggt acattatagt ttgcgactaa gaatgaacca tcgtcaaaca cagcaacaac    6420
tacacccgtg tgaccgatac catatatgct tgcttgtaag tatggcggtt tactagagaa    6480
gccgtaacca acggtaggaa tatgtgttgt tttagcccct aattttttat aaacatacca    6540
cacacgttga ccgtttgtta cttgtccatc atcagttggt tgtcttttc catgtaattg     6600 tgacatatac gcccatgtta attctgtaca ctgaccagca ttaccagttt gagggaatat    6660 gttaccggt ttgtataaat attcttttt gaataaaggt acaccaattg cttttttata      6720
tttttctggt aattggtcat acgtccagtt accacctatc acgaccac ttttccgtt       6780 tggtttcaca gatttacctc taatcgcatt atgctcacca tcgtcatcag tagggtttga    6840
acttccaccg tcatctattt gcacactatc aatgagcttt tttaatgagt cgagtagtcc    6900
aatcgtcatt ttaatatgat acgtgttgtt aaatgttttt tgtagtgtaa aataatcatt    6960
actaaaaaat ttatcactac caatactatg cacgtcccat tgtaatgcgt cttgaacttt    7020
ttttaataat tcttgcatgg cttgttttgc taaagcgagc agtgaactac cactgtcacc    7080
actactacca ctgtcagacg aatcactagg tgaaccacct ttaccgtcta atttaccacc    7140
ccatgctaaa atagtatttg caccgtctaa aaaaggatta ccatagtttt gtactttatt    7200
atatgacgct ttcaaaccta ggggataata tgccgcccaa gtagctgcag ccgttaatgg    7260
gatataagca cgtccaaccg taccagcttt catgttttta gcaaaatctg cattacctt    7320 tctttgtacg ttttgaggta caaagtgaac gatgttacct gcgtcatacc aagacggttg    7380
tcctgcttgt tttgattgtg atacaagctt tctagctaca aatttagcgt ctgttaaata    7440
atcgccttgt gcagaagtat gatttaacca acctaaacct gcactgtatc cttcgttttt    7500
ttcatataca gcaattagcg taggtgaaac tcctatcgat ttaactgcat ttagaacttg    7560
tctgatttta ctttcattac cacctaacca aacattaaaa cgtccataac ctttacttt    7620 aggcactaac tggtctatcg ttaatccaaa gtcatcatta atataagaat gtgtaaattt    7680
atctatcttc tcttggtcgt tcatctttat cactcttttc agaatcgttt ttaattactc    7740
ttaatttatc tttaatttgt tctggcacta atacatccat ctctgcacaa ttttctacaa    7800
tagataaacc ctcattagca atataataga aaatcgtaat cataagtaga ccaccttta    7860 attgtaaaat ttggtcaatg atatttgcta gaataataat acagaatatg agtaattttt    7920
tagcgaaacc tctcattgat ttttttgacc atagattatt atttttaatg gcttttgaaa    7980
tacctgtaat aatatcaaca aacattaata taaataaaaa atatagtaat tttaaatctc    8040
ctgcatatat aaacatgtga aacacttctg tatctgtaaa cctgaatttt acttcattca    8100 ttttttatacc ccctctctaa atttattatt taatggattt tgtaacatag ggttacctga   8160
accatcatta tgccaaaatc tcacaccaga ttccaaaata gcttttaatt gttccattaa    8220
catagggtca atgtcacgta ttgtatacgt acctgtacat tttaaatagt tgcatatagt    8280
catactgtta attggttcaa taaatgtatt atagtcattt acttcaaaac caaacaacat    8340
ataatatttt tgtaaaaatg taatttcttt aggtgacggt acactaattt tcattgttaa    8400
accgttaatg ctatttgcga tttggaaagc gttccccatt tctgactctg tcactgatgg    8460
tggttgtaag gctaaatctt tatattctgc ttgttgttgt ttgtagaaat tatattcttc    8520
attaaactta ccaaataaag cagttggact taaattactt gctacactta cagcgtcata    8580
```

-continued

```
aaaacgtgat tttgggtcac tgccatttaa tacattatct atacgacttg tgattaattg    8640
actttctgca ttacgctgtc tattggcttg ttgtgattgc cctaaaatac cgttattgat    8700
taaaattggt acttgtgcaa aactattaaa tgttatattt gtatttaaga atgaacctgt    8760
atcaattaat atatctttat tttttgcaag tatcggtcta tcattttcag cactgttata    8820
atctactgga taaactcgca cttcattatg ataaccaatg atggattttg tacgtaactt    8880
aacacctgtt ttttgtgaaa tcttaccagc gtcagtaac atagtattac cattccagtc     8940
ataaaaatca atcgtcatgt actcattacg tatcatatgg tcgcactcgt ctttttttaga   9000
caacatcatc tcttgaagct ttgtgaaact taatgataaa tcgtttaaac tccattcttt    9060
tgattttcca ccttgtttta acgtctttaa tccagtaatt ttttcacttg tcttaacgtc    9120
ctctaaatct tttgtattaa tagaatcttt aggtaacatt tgaacctttt gaaagttttg    9180
tgtaatccat ggataggcac tcattttatc cataaagtta ataaagtcac catattccat    9240
aacgtataag ttgactggtg atgtgatatt gtcatatatt gtacctttag acgtatctaa    9300
gtttggctct tttttagtac caaatttctt tgataaatca gcacttgact ggaataacac    9360
taaattttcc aaaaactgtt gcatttggtt atacacatag ttttatttg atactttttaa    9420
cacatcatca ttgttacgta acattggtaa catatagtta tacgtgcgtt ttgataagtg    9480
ttgacgttca atattaacgt ttgagagttg ttctaataca ttaccttgtg tatacgtcat    9540
aatagtatca atcacaaaat atattttaac cacaacatca ttcacatatt cgatttgatt    9600
cacaaacgca taataacgtc tgtcctcaaa atctgataaa aacgtcatgt agttaatccc    9660
ttgtgcgtca tgccactgca tatcaacatt gatttccatt ctatcacgta taaaattata    9720
cggttgtttg gaatagtcta atgatttaaa atgacgtcca tttaaaaaat aatcatcacg    9780
ttcttgatta ctattaaaat gaatcgtatt ttgataatca gtaaacggtg tgttatagaa    9840
aaatttaaaa tttgttaatt ttctcatttt tacctccata aaaaatagtc gtataaatta    9900
tttatacgac tattataaca tttttattca atgatttgtg tatctattgc aaaactttta    9960
ttaccatttg aaagctcact atcactataa tttgatgtaa caaaatgtaa ttcattatta   10020
aagtttaaat ataatcttgt attaatcatt ttcgaatcaa tcgcacattg tgtgtagtga   10080
tgtgtagatt ttaagtttgc gttaatcgta cctaatttaa tatcaccgtt tttcttaatg   10140
ccttttaata ccccttttaa ttgtatggtt ttaacaccat taattgttaa aatacgatat   10200
tgcggtgcag gatatccaac gttgctatca cttgcaataa taccactttc taatgtaata   10260
tcttgccacc ctgtatcatt cacagttgtt ttatttcat taattgtatt taaaatttct    10320
attttatcat tagttattat agcagttaaa ttgttaatac tttgtgtatt attacctaca   10380
ctttcttttg tagctataat atcttgttta ttttttttcaa tatcttcttc atttttttgtg  10440
tttttatcat ctaatatatg aattgcagat tcatgattac ttagtttatt tgtatgttct   10500
gattgaacat ctgataaatt tttttatttt ttatcttgtt gcacattatc ttctttaata   10560
ttaataatgt ctgtagcgtt ttgagaaata ttattttttat ttgtagcgat atcattttta  10620
tttttattaa tgtctttttgt gttcgtatta attttactta ataattcatc tttaaaggtt   10680
aacttataat aatcctcatc acgtcttata taaatgttac cgtcctttgt agtaattaag   10740
tcatttgctt ctactaaatt atcatttaat ttatctacag agtcaatgtt gcgcaaactt   10800
ccttaaaatc caacaaccat tggttaaacc ttttatttta atgttttcca actaattcaa   10860
agaaaaattc tattttatca ttagttttta tagcagttaa attgttaata ctttgtgtat   10920
tattacctac actttctttt gtagctataa tatcttgttt attttttttca atatcttctt  10980
```

```
cattttttgt gtttttatca tctaatatat gaattgcaga ttcatgatta cttagtttat   11040
ttgtatgttc tgattgaaca tctgataaat ttttttatttt tttatcttgt tgcacattat   11100
cttctttaat attaataatg tctgtagcgt tttgagaaat attatttta tttgtagcga    11160 tatcattttt attttttattt atgtcttttg tgttcgtatt aattttactt aataattcat   11220
ctttaaaggt taacttataa taatcctcat cacgtcttat ataaatgtta ccgtcctttg    11280
tagtaattaa gtcatttgct tctactaaat tatcatttaa tttatctaca gagtcaatgt    11340
tgcgcaaact tcttacaatt ctatcagcca ttgtttacac ctcttattta tatcgtttcc    11400
aactaaattc aaagaaaaat cctaaaatac ccattatgag aacacccccc aaggtacacc    11460
aatactatat gcattacctg tttttccgtt ccattgtcta actggtaaat aataacgagt    11520
tccttgccag ttataaccaa tccaaactaa cccatctgat aaacaaactt cgtcatatgg    11580
tgtatagccg tttggttgga accaatagcc attaggttca cttaatttag gactacagac    11640
acgtgcaaat attggtaaaa aaccacatgt aaatgttgcc ttttcgtttc tataatatgt    11700
gccgtattgg ttttgttttcc aattattagt tagttgaata ttttgttcta atactttact    11760
ttcactgttt gagaattttg ggcgaataaa atgtgtcaca ccgtcataat aatgtgttct    11820
aattgttgct ttttcccaac catcatatcc accattcaac cagttttgtt ctaaacatgt    11880
ataataatca agatttccac ttgttacaca ttggatatgt ccatattgag aatttgtgta    11940
tactgcaaca tcacctaatt gaggtttaaa gctcgatgta ttttcataca ccgttgctaa    12000
acctttaaag tcattattaa ttgcgtcttt agcattaccc cacatacgca ctttaccgtc    12060
agtaatataa tagatataag caacagctaa gtccatacat tgaaaaccat atgcaccatc    12120
aaagtcaaca ccaacacctt catgtttata tatccaatct ttagcttgtt gttgtgattt    12180
catttataac actcctatttt tttatgtttt gctacccatt catattcacg atgttttgta    12240
tcagcgttca cattactgaa aaactcttta tattctgata tgttagcttc taatgtttgt    12300
ctcacttctc caactgcgtt accacttgac acacgtaacc atgcaccaac acgttttatt    12360
tcttccggtg cgtctcttgaa taattccatt tggttgcctg taatataata ttctccgggt    12420
gttgtaacgt aagctatcca attattatat ttacttgctt ctaaatattc ttgatatggt    12480
gcgtctgttt tgattgttgt ccataaacca taatcccatt ttaacgtgaa tacatctagc    12540
gtcataccac gctaacttt taccattta cgaccagttg aaaaacgtgt taattcttga    12600
acagtaccta atgtttgtgt tgtagggtat acattaatga aacaaccagc gtcaataatt    12660
tttttacttc catttgtagg catgttttta agcttttctg ccgtactacc gtcaatataa    12720
taaaatccag cttgcgttaa gtcatttaag tcgtcgatat ggtcaggtat agataatgca    12780
cgaccgtcat cttttgttaa tttataattt tgagaacctc ttgcacgtaa tgcttcaaaa    12840
tgttcatatt ctccaagttg gaagaaaccg tataagttat ggaatcgttt accaccaccg    12900
ccattagtca ttgcaagtaa taacgattta cgttttgttt ttgggtttgt ataaatacaa    12960 atacccctcag gctctttaaa attatcacgt gggaagttaa ttccgtcttg gtaagataac    13020
ttaaacgggt aatcgtataa cttttgacca gttgttaatg aatctttgcc aatttgcaca    13080
tgtgaattaa ctgaactgtt accacttaac cagtacaaat catcaccatc aacagcaata    13140
ccttgcatcc aacgtgcatc gttattttct gaattatcaa ttgtcatttc tttttctaca    13200
ttatcaatat gattttttaac atcagctctt gaacgtacct gtatcgtacc atcaccgaaa    13260
cgtaatacga gtttgtcatt tgcttcatca attaacggtg taaaagaatg tttgtttaaa    13320
agtgactgtg gtgtataatc tgttaaccct ttggcttctt ctaaatctaa tacatagtta    13380
```

```
tctttatatg ctacttgcaa cagttttgca acaccatcgt gatgtaacca tattttcatt    13440
tccccgtttg attgtctttc taatccgatt gttgtaccgt gaccaccttg tacaatacgc    13500
atactagaaa ttaaatcacc actaggcgtt aatttattaa tccaaaatcc ctcaggtgtt    13560
tgtgagtcgg attgtgttga gtacatttga ttcgtttctt tatcaatatt aatagattgg    13620
ttcacagcgt tacgaatacc cccaaagccc attacaaact taggttcaag ctcatttaat    13680
tcgaacccat taacaaaacg gttaatgtct ttaattaagt ctttaacttc tgctttaaaa    13740
tcattcattt gtttcatttc agcaacttta aataatgcaa atgcagatgt aagaccggca    13800
ctatatttag taaattcatc atgaataatg ttatctatcg taccatcatt taaccaacct    13860
ctaaataatt ctttagcttg gtctgggaat gctttcatta agtcgtccca attttttgaaa   13920
cgttttttta actcatcgtc atagtcccaa atacgatgtg ctaatacttc aatgagcttt    13980
gataatcttg aaatataatc ataatatgat tttgaattgg tattataatc tgctctatca    14040
tcgtaaaacg gtgtataacg ttctctcgtt ttatatattt cgtctaaaaa tggacgaatg    14100
tcgtcaaaat atttaaaatc gttttcatta tatgccataa ttttccacct ttaccaaatt    14160
tgtaaaaaac atttttttat caaattcatt taaaattttc tttcttaaat cgtatacttt    14220
atcaatatta tcaattaaat actgttttga aaattgtgtg cctttcgcat taccttttg     14280
attttgatta cgttttacgt tttgattact ttcgttactt gatttattca cagttttacc    14340
gttatcaatc gtgttattgt ctgcaaattt taacgttgtt ttatctacat caatgttaac    14400
ctcgctttgt ggtaatgaca cataagcatt tctgttcgct gtcataccag ttgaattgtc    14460
taaagatgta gcattttgat ttgatgtttc atctgtgttg tttgttgtat cttcattatg    14520
ttctgtaaaa ccttgtgatt gtagatattt tcaacttca cttgatgaat aaacaacatt     14580
caaataatcc tcatgtgtga tacatacagt aatcacttgc ataccaaatg cctcaactgt    14640
ttgtctgtta atctctctat ctaaaaaatg aatcgtaaat gattttttaa aaagtaagtc    14700
tgataaatct tctttcaatg aaaaacccttt aaatactttt tcattaacga tagctaaaac   14760
atctttatcg aatttcaaca tttttttgcat aaattgaaaa tcatcatcat aaaacgttaa    14820
tttattatca tttacaaatt cattgaaacc ttttttaata agctcagatt taataaaatc    14880
gtataaagtc attgtatatc tagccattta aatcactact ttcatctttt aaaagtgtgt    14940
caaccattga tattttagac gttgtttcat catcgtaata cggtttaata tctaaaccat    15000
agcgtttaga taaaaacgtg attggttcac gacctttaa ataaatatta ctatttgatg      15060
ttgtaaaacc acgattactt ttagcttctt catctgatac accactttct ttatcaacag    15120
ctaaagagtt aatacctaaa tagttactta attcactaat cttattttga tactctcttt    15180
tcatctcagt taaagcagga atcacactat tacttgttaa atcaataatg tcatcttctg    15240
cattaaacat aggtgacatt ttaacaaatg gtgcaccgtt atatatttct gatacaagtt    15300
gattaattga ctcgtcatta atttctgatt taaataccct tgctaaattc gcttgcataa    15360
tcaatgaaaa tcgagataaa acaacttcag ctaattcatc ggtatagtgt tcaatgattt    15420
caatatcact attatactgt ataggtttat tttgcataac aacaaagtta ccactcatac    15480
aattatcgta tagcttatga atttgtagac actcatcagg aattaaatag tcaggtacaa    15540
taaaataaat atcttctttt gttaatcgtt tttgaaattg gaaattaaag tttgatgaaa    15600
aatttggtgc ttgattaaaa taggtattat ttacataacc aagtatcata atttgtttat    15660
ttctagcttc accaaccact acattaatat tttgccttaa tgcagactct aactgtataa    15720
aatctatacc aaccgtatca cgattggtat agtttataag taggggtaaa aattccaaat    15780
```

```
aacgattaaa cataagacgt ttaaatctgt tgcgatgttc aacaactctt ttgttgattt   15840
cttttgataa ttcaacgttt aaacctcttt tatcgttgtt catatttacg ctccttttat   15900
tctgttgctt cttcctctag ttttggtgtt acatcttggt cagtaattaa tattttatta   15960
aagaatggac taatagcctt gaatgaataa taatgaatcc agtgtgtgac ctcatcaaat   16020
tcaccattat agaatggttg ttttaacata cctttggtat aacgtttgta tttaattgca   16080
ttaatatcta aaataaatgc gtataaatct gattttggtt taatttcttc aatgttacca   16140
gtaaactctt taagtttaga aacatcataa gtaaatactg caccaactgg aattgtgtca   16200
ccaatttgcg actgataatc accgtaagca cgtaagaaat caattgtctc ttgattttgt   16260
aatttaaatt cttttgttac tttaaacaca ccacctaaat catcaaaact tataacatgg   16320
tctgtaaaat caataccagc gatttggaat gtgttagcaa ttttgtatc taataggtaa    16380
gattttaaag aatctgttgt taaaataaca atatctttta acttagatac agttgtatat   16440
tgaccaattg caccaccaga agcacggtga acttcattgt atttagcgct gttgttttgt   16500
aagtttaaaa ttgcttcaaa tactttgctt gctaaatctt cttttgatgt tgttttacgt   16560
acgtttgact ctgataattg atttaatgag taatcaacta acattgctcg catttctttt   16620
tcttctaata cattaatatc agaaattttc tttttatata cacctaatgc gtaatttgtt   16680
gcgtctgcta atgtttggaa attgaaacgt gtatcattat tgtttaatgt gaattttttgt  16740
ttcttcacaa taccactacc atataactta gtagccatac gtggataatt acgtttcaac   16800
attaattcct cattttttga taaatccata ttaattggta ctgtatccat aatgacatat   16860
tcttcactat attgaccaat aaagtcttgt tctttagcta accaattaaa acggttacct   16920
aaagcaatat caattaataa tgtctcgtta atcttaggga ataaatattt atttacaaat   16980
gtttcaaaca ttgtattatt gttatcccat ttatcaccaa atgtccaaga ttttgaataa   17040
tcatggttaa aatcttgtaa tgccgacttt gcagattttg ctactaaaag agctgtttcg   17100
ttttttgtac ttgctggtgc cataaatttat tattcctcct ctacgtctcc gctaaaagtt   17160
tgttttgaaa gtgaatggat ttgtacaccg tactcatctt cacttttgtt tacatctatt   17220
gacatatttt catttaattc agtacgttta tttaaacgtg aatcttcata tgatgtcccc   17280
atcatagaac gcatgttatt gccttcatac atattatttt cctcctaatc taaatctaac   17340
ttgtcaacta attcttcatc tgaatagtct ttatcttctt tgtcagcatt tgttacatct   17400
ggttgtgttt gttgtggttg ttgaatttgt gatgataaaa aagtagtcat tgttgctct    17460
aatgatgtaa tacgttgttc taatataaca gggtcgaatt ttgaactatc ttcatctgtt   17520
atagtaggtt ctaatttatt cttatttct tcttcaattg tttctactgt tttatcttca   17580
gtaggttctt cagttggttc ttcagttggt tcttcagttg gttctttgtc gtctggtttt   17640
acgatttcct caaattctgt cattgtgaca cctccaaaat attttataac taattatatc   17700
atagaatatt taaataagta aattaaattt attaaaaagc gtgaacatag ttttcaataa   17760
aagtaaatag atgtatatat tttgtaatta atgaatatgt aataggttag ataagttgga   17820
aaagtaggtg aacattttt ataagtttag tttagaaatg ataagttaat ttataagttt    17880
tgatttgtat aatcgtttat tttaaacggt ggggaggtgt aaatttacaa aaactttt    17938
```

<210> SEQ ID NO 2
<211> LENGTH: 750
<212> TYPE: DNA
<213> ORGANISM: Antimicrobial gene
<220> FEATURE:
<221> NAME/KEY: gene
<222> LOCATION: (1)..(750)
<223> OTHER INFORMATION: Antimicrobial Protein

<400> SEQUENCE: 2

```
atgaaatcac aacaacaagc taaagattgg atatataaac atgaaggtgt tggtgttgac    60
tttgatggtg catatggttt tcaatgtatg gacttagctg ttgcttatat ctattatatt   120
actgacggta aagtgcgtat gtggggtaat gctaaagacg caattaataa tgactttaaa   180
ggtttagcaa cggtgtatga aaatacatcg agctttaaac ctcaattagg tgatgttgca   240
gtatacacaa attctcaata tggacatatc caatgtgtaa caagtggaaa tcttgattat   300
tatacatgtt tagaacaaaa ctggttgaat ggtggatatg atggttggga aaaagcaaca   360
attagaacac attattatga cggtgtgaca cattttattc gcccaaaatt ctcaaacagt   420
gaaagtaaag tattagaaca aaatattcaa ctaactaata attggaaaca aaaccaatac   480
ggcacatatt atagaaacga aaaggcaaca tttacatgtg ttttttacc  aatatttgca   540
cgtgtctgta gtcctaaatt aagtgaacct aatggctatt ggttccaacc aaacggctat   600
acaccatatg acgaagtttg tttatcagat gggttagttt ggattggtta taactggcaa   660
ggaactcgtt attatttacc agttagacaa tggaacggaa aaacaggtaa tgcatatagt   720
attggtgtac cttgggggt gttctcataa                                     750
```

<210> SEQ ID NO 3
<211> LENGTH: 249
<212> TYPE: PRT
<213> ORGANISM: Antimicrobial Protein

<400> SEQUENCE: 3

```
Met Lys Ser Gln Gln Gln Ala Lys Asp Trp Ile Tyr Lys His Glu Gly
  1               5                  10                  15

Val Gly Val Asp Phe Asp Gly Ala Tyr Gly Phe Gln Cys Met Asp Leu
             20                  25                  30

Ala Val Ala Tyr Ile Tyr Tyr Ile Thr Asp Gly Lys Val Arg Met Trp
         35                  40                  45

Gly Asn Ala Lys Asp Ala Ile Asn Asn Asp Phe Lys Gly Leu Ala Thr
     50                  55                  60

Val Tyr Glu Asn Thr Ser Ser Phe Lys Pro Gln Leu Gly Asp Val Ala
 65                  70                  75                  80

Val Tyr Thr Asn Ser Gln Tyr Gly His Ile Gln Cys Val Thr Ser Gly
                 85                  90                  95

Asn Leu Asp Tyr Tyr Thr Cys Leu Glu Gln Asn Trp Leu Asn Gly Gly
            100                 105                 110

Tyr Asp Gly Trp Glu Lys Ala Thr Ile Arg Thr His Tyr Tyr Asp Gly
        115                 120                 125

Val Thr His Phe Ile Arg Pro Lys Phe Ser Asn Ser Glu Ser Lys Val
    130                 135                 140

Leu Glu Gln Asn Ile Gln Leu Thr Asn Asn Trp Lys Gln Asn Gln Tyr
145                 150                 155                 160

Gly Thr Tyr Tyr Arg Asn Glu Lys Ala Thr Phe Thr Cys Gly Phe Leu
                165                 170                 175

Pro Ile Phe Ala Arg Val Cys Ser Pro Lys Leu Ser Glu Pro Asn Gly
            180                 185                 190

Tyr Trp Phe Gln Pro Asn Gly Tyr Thr Pro Tyr Asp Glu Val Cys Leu
        195                 200                 205
```

```
Ser Asp Gly Leu Val Trp Ile Gly Tyr Asn Trp Gln Gly Thr Arg Tyr
    210             215             220

Tyr Leu Pro Val Arg Gln Trp Asn Gly Lys Thr Gly Asn Ala Tyr Ser
225             230             235             240

Ile Gly Val Pro Trp Gly Val Phe Ser
                245
```